US006194612B1

(12) United States Patent
Boger et al.

(10) Patent No.: US 6,194,612 B1
(45) Date of Patent: Feb. 27, 2001

(54) TEMPLATE FOR SOLUTION PHASE SYNTHESIS OF COMBINATION LIBRARIES

(75) Inventors: Dale L. Boger, La Jolla; Soan Cheng, San Diego; Peter L. Myers, Orinda, all of CA (US)

(73) Assignees: The Scripps Research Institute, LaJolla; CombiChem, Inc., San Diego, both of CA (US)

( * ) Notice: Subject to any disclaimer, the term of this patent is extended or adjusted under 35 U.S.C. 154(b) by 0 days.

(21) Appl. No.: 09/056,385

(22) Filed: Apr. 7, 1998

Related U.S. Application Data

(62) Division of application No. 08/732,042, filed on Oct. 16, 1996, now abandoned.
(60) Provisional application No. 60/006,891, filed on Oct. 17, 1995.

(51) Int. Cl.[7] ...................... C07C 231/00; C07C 233/00; C07C 235/00; C07C 237/00; C07C 239/00; G01N 33/53; G01N 33/566; A61K 38/00; C07K 5/00

(52) U.S. Cl. ................... 564/133; 435/7.1; 435/DIG. 50; 436/501; 436/518; 436/536; 530/334; 562/869; 562/887; 564/152; 564/155; 564/159; 564/163; 564/166; 564/168; 564/169; 564/180; 564/185; 564/186; 564/193; 564/194; 564/195; 564/196; 564/197; 564/199; 564/200

(58) Field of Search .............................. 435/7.1, DIG. 50; 436/501, 518, 536; 562/869, 887; 530/334; 564/133, 152, 155, 159, 163, 166, 168, 169, 180, 185, 186, 193–197, 199, 200

(56) References Cited

U.S. PATENT DOCUMENTS

| 4,058,610 | * | 11/1977 | Cox et al. | 424/246 |
| 5,635,598 | * | 6/1997 | Lebl et al. | 530/334 |
| 5,767,238 | * | 6/1998 | Caporale | 530/334 |

OTHER PUBLICATIONS

March, J. Advanced Organic Chemistry: Reactions, Mechanisms and Structure, 4th Ed. 1992. New York; John Wiley & Sons, pp. 418–421.*

Cathala et al. "Macrobicyclic and Macrotricyclic Tetralactams with 1,10–Phananthroline Units. Dinuclear Eu3+ Cryptate of the Macrotricyclic Ligand". Tetrahedron Letters, vol. 35, No. 12, pp. 1863–1866, 1994.*

* cited by examiner

Primary Examiner—Jyothsna Venkat
Assistant Examiner—Maurie E. Garcia
(74) Attorney, Agent, or Firm—Welsh & Katz, Ltd.

(57) ABSTRACT

This invention features a template for synthesizing combinatorial libraries, methods of synthesizing combiatorial libraries of chemical compounds utilizing the template, and combinatorial libraries of chemical compounds formed by the methods of this invention.

3 Claims, 11 Drawing Sheets

TEMPLATE FOR SOLUTION PHASE SYNTHESIS OF COMBINATION LIBRARIES

RELATED APPLICATIONS

The instant application is a divisional of U.S. patent application Ser. No. 08/732,042, filed Oct. 16, 1996, now abandoned, the disclosure of which is hereby incorporated by reference in its entirety. This application claims priority to Boger et al., TEMPLATE FOR SOLUTION PHASE SYNTHESIS OF COMBINATORIAL LIBRARIES, U.S. Provisional Application No. 60/006,891, filed Oct. 17, 1995, which is incorporated herein by reference including drawings.

BACKGROUND OF THE INVENTION

Two approaches have been used in efforts to discover novel chemicals useful in medicine, agriculture, or basic research. In the first approach of rational design, researchers perform structural studies to determine the three-dimensional structure of a target molecule in order to design compounds which are likely to interact with that structure. In the second approach, large libraries of compounds are screened for a desired biological activity. Compounds exhibiting activity in these screening assays become lead chemical compounds. Further study of compounds with structural similarity to the lead compounds can then lead to the discovery of other compounds with optimal activity.

Although traditional screening assays have focused on the screening of naturally occurring compounds, the ability to synthesize large combinatorial libraries of compounds with diverse structures has greatly increased the number of compounds available for screening. In combinatorial chemistry, each reactant from a first group of reactants is reacted with each reactant from a second group of reactants to yield products containing all the combinations possible from the reaction. If desired, all of the products from the first reaction are then reacted with each reactant from a third group of reactants to yield a large array of products. Additional reactions, if desired, can further increase the size of the library of compounds. Where it is desirable to use protection/deprotection protocols to prevent reactive groups from participating in a given reaction step, typically the same protocols are used for each compound in the growing library.

The generation and use of combinatorial chemical libraries for the identification of novel lead compounds or for the optimization of a promising lead candidate has emerged as a promising and potentially powerful method for the acceleration of the drug discovery process. (Terrett, N. K., et al., Tetrahedron 51:8135 (1995); Gallop, M. A., et al., J. Med. Chem. 37:1385 (1994); Janda, K. D., Proc. Natl. Acad. Sci. U.S.A. 91:10779 (1994); Pavia, M. R. et al., Bioorg. Med. Chem. Lett. 3:387 (1993)).

Initial studies focused on the synthesis of peptide or oligonucleotide libraries and related oligomeric structures. (See Gallop, supra, Geysen, H. M., et al., Proc. Natl. Acad. Sci. U.S.A. 81:3998 (1984); Lam, K. S., et al., Nature 354:82 (1991); Houghten, R. A., et al., Nature 354:84 (1991); Salmon, S. E. et al., Proc. Natl. Acad. Sci. U.S.A. 90:11708 (1993); Owens, R. A., et al., Biochem. Biophys. Res. Commun. 181:402 (1991); Bock. L. C., et al., Nature 355:564 (1992); Scott, J. K. and Smith, G. P., Science 249:386 (1990); Cwirla, S. E., et al., Proc. Natl. Acad. Sci. U.S.A. 87:6378 (1990); Devlin, J. J., et al., Science 249:404 (1990); Simon, R. J., et al., Proc. Natl. Acad. Sci. U.S.A. 89:9367 (1992); Zuckermann, R. N., et al., J.Am. Chem. Soc. 114:10646 (1992); Miller, S. M., et al., Bioorg. Med. Chem. Lett. 4:2657 (1994); Zuckerman, R. N., et al, J. Med. Chem. 37:2678 (1994); Terrett, N. K., et al., J. Bioorg. Med. Chem. Lett. 5::917 (1995); Cho, C. Y., et al., Science 261:1303 (1993); Winkler et al, WO93/09668 (PCT/US92/10183)); Ostresh, J. M., et al., Proc. Natl. Acad. Sci. U.S.A. 91:11138 (1994).

Because many ligands for biologically important receptors are non-peptide ligands, and because non-peptide compounds can mimic or block the effects of peptide ligands as well as non-peptide ligands, more recent efforts have been directed at exploiting the greater diversity and range of useful properties embodied in more conventional small molecule libraries. (See. e.g., Simon, R. J., et al., Proc. Natl. Acad. Sci. U.S.A. 89:9367 (1992); Zuckermann, R. N., et al., J.Am. Chem. Soc. 114:10646 (1992); Miller, S. M., et al., Bioorg. Med. Chem. Lett. 4:2657 (1994); Zuckerman, R. N., et al, J. Med. Chem. 37:2678 (1994); Terrett, N. K., et al., J. Bioorg. Med. Chem. Lett. 5::917 (1995); Cho, C. Y., et al., Science 261:1303 (1993); Winkler et al, WO93/09668 (PCT/US92/10183)); Ostresh, J. M., et al., Proc. Natl. Acad. Sci. U.S.A. 91:11138 (1994); Bunin, et al., J. Am. Chem. Soc. 114:10997 (1992); Bunin, et al., Proc. Natl. Acad. Sci. U.S.A. 91:4708 (1994); Virgilio, A. A. and Ellman, J. A., J. Am. Chem. Soc. 116:11580 (1994); Kick, E. K., and Ellman, J. A., J. Med. Chem. 38:1427 (1995); DeWitt, S. H., et al., Proc. Natl. Acad. Sci. U.S.A. 90:6909 (1993); Chen, C., et al., J. Am. Chem. Soc. 116:2661 (1994); Beebe, X., et al., J. Am. Chem. Soc. 114:10061 (1992); Moon, H. -S., et al., Tetrahedron Lett. 35:8915 (1994); Kurth, M. J., et al., J. Org. Chem. 59:5862 (1994); Gordon, D. W., and Steele, J., J. Bioorg. Med. Chem. Lett. 5;47 (1995); Patek, M., et al., Tetrahedron Lett. 35:9169 (1994); Patek, M., et al., Tetrahedron Lett. 36:2227 (1995); Campbell, D. A., et al., J. Am. Chem. Soc. 117:5381 (1995); Forman, F. W., and Sucholeiki, I., J. Org. Chem. 60:523 (1995); Rano, T. A, and Chapman, K. T., Tetrahedron Lett. 36:37879 (1995); Dankwardt, S. M., et al., Tetrahedron Lett. 36: 4923 (1995); Deprez, B., et al., J. Am. Chem. Soc. 117:5405 (1995); Ellman, U.S. Pat. No. 5,288,514).

A range of approaches to the synthesis of diverse chemical libraries have been disclosed including several methods utilizing solid supports. In solid support synthesis, a first reactant is linked to a solid support. This linkage may include a spacer linker arm connecting a functional group on the first reactant to a functional group on the solid support. Reaction of the first reactant bound to the solid support with a second reactant produces a desired product which is bound to the solid support, while unreacted second reactant remains unbound in solution. If desired, additional reactants can be added to the product of the first reaction in subsequent reactions.

Solid phase synthesis has been adapted from solid phase synthesis of peptides and oligonucleotides for use in the synthesis of small chemical libraries. Methods of synthesizing diverse chemical libraries on solid supports include split or mixed synthesis (Furka, A., et al., Abst. 14th Intl. Congress Biochem., Prague 5:47 (1988); Furka, A., et al., Int. J. Peptide Protein Res. 37:487 (1991); Houghten, R. A., Proc. Natl. Acad. Sci. U.S.A. 82:5131 (1985)); Erb, E., et al., Proc. Natl. Acad. Sci. U.S.A. 91:11422 (1994)), encoded synthesis (Brenner, S., and Lerner, R. A., Proc. Natl. Acad. Sci. U.S.A. 89:5381 (1992); Nielsen, J., et al., J. Am. Chem. Soc. 115:9812 (1993); Needels, M. C., et al., Proc. Natl. Acad. Sci. U.S.A. 90:10700 (1993); Nikolaiev, V., et al., Peptide Res. 6:161 (1993); Kerr, J. M., et al., J. Am. Chem. Soc. 115:2529 (1993); Ohlmeyer, M. H. J., et al., Proc. Natl.

Acad. Sci. U.S.A. 90:10922 (1993); Nestler, et al., J. Org. Chem. 59:4723 (1994); Baldwin, J. J., et al., J. Am. Chem. Soc. 117:5588 (1995)), indexed synthesis (Pirrung, M. C. and Chen, J., J. Am. Chem. Soc. 117:1240 (1995); Smith, P. W., et al., Bioorg. Med. Chem. Lett. 4:2821 (1994)), or parallel and spatially addressed synthesis on pins (Geysen, et al., Proc. Natl. Acad. Sci. U.S.A. 81:3998 (1984); DeWitt, S. H., et al., Proc. Natl. Acad. Sci. U.S.A. 90: 6909 (1993)), beads (Merrifield, R. B., J. Am. Chem. Soc. 85:2149 (1963)), chips (Fodor, S. P. A., et al., Science 251: 767 (1991)), and other solid supports (Atherton, E. and Sheppard, R. C., *Solid Phase Peptide Synthesis: A Practical Approach* (IRL Press: Oxford, 1989); Grubler, G., et al., in *Peptides: Chemistry, Structure, and Biology* (Proceedings of the Thirteenth American Peptide Symposium) (Hodges, R. A. and Smith, J. A., Eds., ESCOM-Leiden, The Netherlands, 1994) at 51; Englebretsen, D. R. and Harding, D. R. K., Int. J. Peptide Protein Res. 40:487 (1992); Frank, R., Bioorg. Med. Chem. Lett. 3:425 (1993); Frank, R. and Doring, R. Tetrahedron 44:031 (1988); Schmidt. M., et al., Bioorg. Med. Chem. Lett. 3:441 (1993); Eichler, J., et al., Peptide Res. 4:296 (1991)).

Some of the features of solid phase synthesis responsible for its widespread use in chemical synthesis are its repetitive coupling reactions as well as ease of product isolation and sample manipulation. Because the growing product is bound to the solid support, unreacted reactants can be easily removed by washing and/or filtration after each reaction in the synthesis of the final product. Furthermore, because of the ease of removal of unreacted reactants, the synthesis and separation of product from unreacted reactants can be automated. In addition, the ability to isolate the resin bound product by simple filtration permits the use of large reagent excesses to obtain high yields which are required for each step of a multistep synthesis.

In part, because of these features of solid phase synthesis, solution phase combinatorial synthesis has not yet gained wide acceptance as an alternative to solid phase synthesis. There have been, however, recent reports of solution phase, single-step amide, ester or carbamate condensations in the preparation of library mixtures. (Pirrung, M. C. and Chen, J. J. Am. Chem. Soc. 117:1240 (1995); Smith, P. W., et al., Bioorg. Med. Chem. Lett. 4:2821 (1994); Peterson, J. B. in *Exploiting Molecular Diversity: Small Molecule Libraries for Drug Discovery*, La Jolla, Calif., (Jan. 23–25, 1995). For the introduction of soluble polymer supports, see Han, H., et al., Proc. Natl. Acad. Sci. U.S.A. 92:641(1995)). Methods for carrying out liquid phase synthesis of libraries of peptides and oligonucleotides coupled to a soluble oligomeric support have been described. (Bayer, Ernst and Mutter, Manfred, Nature 237:512–513 (1972); Bayer, Ernst, et al., J. Am. Chem. Soc. 96:7333–7336 (1974); Bonora, G. M., et al., Nucleic Acids Res. 18:3155–3159 (1990)). In oligomer-supported liquid phase synthesis the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, as well as eliminating tedious purification steps associated with traditional liquid phase synthesis. oligomer-supported liquid phase synthesis has also been adapted to automatic liquid phase synthesis of peptides. (Bayer, Ernst, et al., *Peptides: Chemistry, Structure, Biology*, 426–432).

Liquid phase synthesis also has features which make it attractive for use in chemical synthesis. Liquid phase synthesis does not have the restrictions of scale of reaction imposed by high cost and difficulty in handling large amounts of solid support necessary to obtain large quantities of product. Liquid phase synthesis also eliminates the requirement for the presence of functional groups on the first reactant and the solid support for attachment of the reactant to the solid support or soluble oligomer. (Pirrung, M. C., and Chen, J., *J. Am. Chem. Soc.* 117:1240 (1995); Smith, P. W., et al., *Bioorg. Med. Chem. Lett.* 4:2821 (1994)). In addition, the use of liquid phase synthesis also avoids the requirement for compatible spacer linkers. Moreover, liquid phase synthesis, unlike solid phase synthesis, does not require limited reaction chemistries to avoid detachment of the growing product from the solid support, or orthogonal attachment and detachment chemistries which often result in the release of spectator functional groups.

Liquid phase synthesis also does not require the use of specialized protocols for monitoring the individual steps of a multistep solid phase synthesis. (Egner, B. J., et al., J. Org. Chem. 60:2652 (1995); Anderson, R. C., et al., J. Org. Chem. 60:2650 (1995); Fitch, W. L., et al., J. Org. Chem. 59:7955 (1994); Look, G. C., et al., J. Org. Chem. 49:7588 (1994); Metzger, J. W., et al., Angew. Chem., Int. Ed. Engl. 32:894 (1993); Youngquist, R. S., at al., Rapid Commun. Mass Spect. 8:77 (1994); Chu, Y. -H., et al., J. Am. Chem. Soc. 117:5419 (1995); Brummel, C. L., et al., Science 264:399 (1994); Stevanovic, S., et al., Bioorg. Med. Chem. Lett. 3:431 (1993)). In solid phase synthesis, immobilized reactants which fail to react cannot be separated from immobilized reaction product intermediates. If the unreacted reactants participate in later reactions, they will give rise to a different undesired product than the intermediates, and the desired product will be released in an impure state. Thus, to be useful, each reaction in a solid phase synthesis must proceed with an unusually high efficiency. Optimization of the reactions to obtain the required reaction efficiencies is both time consuming and challenging. Even a modest level of purity in the final product (85%) pure requires a 92% yield at each step of a two-step reaction sequence, and a 95% yield at each step of a three-step reaction sequence. These high yields are not routinely available and require both an extensive investment in reaction optimization and/or a purification of the released solid phase product at each step. In addition, it may be necessary to use capping reactions at each step of the reaction to prevent the unreacted reactant from participating in subsequent reactions.

Because intermediates are not immobilized in liquid phase synthesis, liquid phase synthesis permits ease of sample manipulation and the purification of intermediates at each step. The non-limiting scale, expanded and nonlimiting repertoire of chemical reactions, direct production of soluble intermediates and final products for assay or for purification, and the lack of required linking, attachment/detachment or capping strategies make solution phase combinatorial synthesis an attractive alternative to solid phase synthesis.

None of the references described herein is admitted to be prior art.

SUMMARY OF THE INVENTION

This invention relates generally to compounds which can serve as a template for the synthesis of combinatorial libraries, methods of synthesis of combinatorial libraries utilizing a template, and the combinatorial libraries produced by such methods.

One remaining limitation to solution phase parallel synthesis of combinatorial libraries is the separation of products from unreacted reactants and reagents. It is therefore of interest to develop reagents and methods for solution phase synthesis of combinatorial libraries in which reaction products can be easily separated from unreacted reactants. In addition, in order to adapt solution phase chemistry to combinatorial synthesis, protocols for solution phase combinatorial synthesis are required. Once protocols for synthesis and methods of purification are available, liquid phase combinatorial synthesis will be convenient and easily automated.

In a first aspect, this invention features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptide ligands or peptide ligands.

A compound which has one or more characteristics in common with a peptide is said to be "peptidomimetic", and may include non-natural peptide linkages. Such characteristics may include a molecular conformation similar to that of a peptide; for example, a molecular backbone structure or similar functional properties to that of a peptide, such as the ability to bind to and activate or block a particular cellular receptor. In addition, some compounds which contain peptidomimetic structures may also mimic non-peptide ligands. However, unlike peptides, when orally administered the peptidomimetic compounds of the present invention may be resistant to degradation by hydrolysis or proteolysis, and survive rapid metabolism once absorbed systemically. Peptidomimetic compounds of the combinatorial library produced using the template may therefore be more suitable for oral administeration than peptides.

A template refers to a chemical compound having a densely functionalizable core. The densely functionalizable core may be symmetrical and impose little structural or conformational bias. Alternatively, it may be desirable for the densely functionalizable core to be asymmetrical so that the functionalization reactions will be regiospecific and/or stereospecific.

A densely functionalizable core is a chemical group which contains two or more functionalization sites attached to nearby atoms within the template. By "nearby atom" is meant preferably within 1 to 10 atoms, more preferably 1 to 6, even more preferably 2 to 5 atoms.

A reactant containing a functional group is capable of reacting with a functionalization site on the template. The reactants added to the functionalization sites of the template core provide molecular diversity and, as such, libraries built upon a template may prove widely applicable to many, if not all, biological targets.

Chemical modification of the template or core molecule results in the generation of a "multifunctionalized core molecule" or "multifunctionalized product". A "multifunctionalized product" is a template molecule which has been reacted with two or more reactants, each containing a functional group capable of reacting with a functionalizable group on the template, wherein the functional groups may be the same or different from each other. Furthermore, a reactant may contain an additional functionalizable group blocked with a protecting group.

The multifunctionalized product is functionally equivalent to a multi-subunit compound. For instance, where a template has been reacted with three reactants the multifunctionalized product is functionally equivalent to a three subunit compound, such as a tripeptide, without the need for protection and deprotection steps. This is in contrast to typical methods of synthesis of peptides in which, due to the need for protection and deprotection steps, the synthesis of a trimer containing three subunits would require six to nine steps.

A template to which one reactant has been added to one functionalization site is referred to as a "first-modified product." A template to which reactants have been added to two functionalization sites is referred to as a "second-modified product." A template to which three reactants have been added to three functionalization sites is referred to as a "third-modified product". A template to which more than three reactants have been added is similarly referred to by the term "n-modified product", where n is the number of reactants which have been added to functionalization sites on the template, including functionalization sites introduced during earlier reactions.

Preferably the template will contain three functionalization sites which can be differentially reacted with reactants containing functional groups.

A reactant is any chemical which can undergo a chemical reaction to form a new bond. Because the functionalization sites, reactants and the reaction conditions are not limited, templates can be designed for use with a very broad spectrum of chemical reactions. Because of the variability permitted by the choice of reactants, use of a template having three functionalization sites enables the synthesis of combinatorial libraries with at least three variable groups. Where at least one reactant contains additional groups which can serve as functionalization sites, the compounds in a combinatorial library synthesized using a template initially containing three functionalizable groups may have more than three variable groups.

Preferably, the reactant will be selected from nucleophiles or electrophiles, such as acylating agents, amines, carboxylic acids, amides, esters, thioesters, L-amino acids, D-amino acids, synthetic amino acids, nucleotides, sugars, lipids, or carbohydrates. In addition, the reactants may contain additional chemical groups such as a carbon-hetero multiple bond, heterocycles, ethers, aromatic groups, or a group which can act as an additional functionalization site. Where the reactant contains a group which can act as an additional functionalization site, preferably the functionalizable group will not be reactive in the reaction in which the reactant is added to the template. For instance, the additional functionalizable group may be blocked by a protecting group such as BOC or Fmoc, or may be less reactive than the functional group undergoing reaction. For instance, primary amines are more reactive than alcohols.

Where the functionalization site is an electrophile, e.g., an anhydride or other activated carboxylic acid derivative, the reactant will be a nucleophile. An electrophile is a chemical compound which is seeking electrons. A nucleophile is an electron rich compound, and may carry a formal charge or be partially charged through polarization of a chemical bond. Even more preferably, the nucleophile will be an alcohol [$R^1OH$], amine [$R^1N(R^2)R^3$], thiol [$R^1SH$], where R1, R2 and R3 may be the same or different, cyclic or acyclic and optionally substituted; may be, for example, hydrogen, alkyl, alkenyl, alkynyl, ether, heterocyclic, or aryl; and X is a halide such as fluorine, chlorine or bromine. Still more preferably, the reactant will be a primary amine [$R^1NH_2$]. Preferably R1, R2, and R3 will contain 1–15 carbon atoms, more preferably 1–12 carbon atoms, even more preferably 1–10 carbon atoms.

Where the functionalization site is a nucleophile, the functional group on the reactant will be an electrophile, for example, an acylating agent. An electrophile may be, for example, azide, halide, active ether, aryl halide, or an activated carboxylic acid derivative such as a carboxylic acid halide, or ester. Preferably an acylating agent will contain, for example, at least one of the following chemical groups: an activated carboxylic acid derivative, a chloroformate, an isocyanate, a sulfonyl halide such as a sulfonyl chloride, an acid halide such as an acid chloride, or a phosphonate. More preferably, the functional group will be an activated carboxylic acid derivative. Preferably the electrophilic reactant will contain 1–15 atoms, more preferably 1–12 atoms, and even more preferably 1–10 atoms.

Functionalization site refers to a chemical group capable of undergoing a chemical reaction with a functional group of a reactant in which a bond is formed between the functionalization site and the functional group on the reactant. A functionalization site may be present as a reactive functionalization site which is capable, without an additional chemical reaction, of reacting with a reactant. Alternatively, a functionalization site may be present in an unreactive form which is attached to a blocking group in order to prevent reaction of the functionalization site in a given reaction step. The blocking group can be removed prior to a later reaction step, liberating the functionalization site in a reactive form suitable for reaction with a reactant. The activated form of the functionalization site is preferably a nucleophile or an electrophile. Even more preferably, the functionalization site is an electrophile containing a carbonyl group. Alternatively, even more preferably a functionalization site will be a nucleophile containing an amine.

Still more preferably, where the functionalization site is an electrophile, the functionalization site may be an activated carboxylic acid derivative or an anhydride. An anhydride contains both a reactive functionalization site, and a protected functionalization site which is released upon reaction of the anhydride to yield a functionalized acyl group and a carboxylate functionalization site. For purposes of this application, an anhydride chemical group will be considered to contain two functionalization sites.

In a second aspect, this invention features a method of liquid phase combinatorial synthesis utilizing a template, which includes the following steps:

(a) reacting one functionalization site of the template with at least one reactant;

(b) repeating step (a) at least once.

The reaction between a functionalization site and a reactant is an organic chemical reaction. Preferably, where the functionalization site is electrophilic, the reaction will be a nucleophilic acyl substitution.

The bond formed by the chemical reaction may be, for example, ester $[R^1C(O)OR^2]$, thioester $[R^1C(O)SR^2]$, or amide $[R^1C(O)N(R^2)R^3]$ (where each $R^1$, $R^2$, and $R^3$ may be the same or different, cyclic or acyclic; may be, for example, hydrogen, alkyl, alkenyl, alkynyl, ether, heterocyclic, or aryl. Where the functionalization site is a nucleophilic group, the reaction will preferably be an acylation reaction. Preferably the bond formed by the chemical reaction will be an amide.

The chemical synthesis will preferably involve two or more sequential reaction steps. Preferably, at each step, one reactant forms a bond with one functionalization site on the template. In addition, reactants may contain additional functionalization sites which participate in additional reaction steps with additional reactants. A reaction step refers to one reaction in a series of reactions.

At each reaction step, preferably aliquots of template will be individually reacted with a set of reactants to form a set of n-modified multifunctionalized products.

Preferably, separation of desired products from unreacted reactant and other reagents is performed following each reaction, before proceeding to the next reaction step. Preferably this separation is a liquid phase/liquid phase extraction or a solid phase/liquid phase extraction. To facilitate either liquid/liquid or solid/liquid extractions, it is preferred that there is a difference in charge or polarity or hydrophobicity between the desired product and the unreacted reactant. For instance, the desired product may be uncharged while the unreacted reactants are charged, or the desired product may be charged while the unreacted reactants are uncharged. An adjustment of the pH of the reaction mixture may be necessary to obtain this charge difference.

In liquid/liquid extractions, a liquid phase which is immiscible with the reaction mixture is then added to the reaction mixture. For example, if the reaction solution is hydrophobic and nonpolar, a given specific volume of a polar acqueous phase is added to the reaction mixture. Unless highly polar, the neutral, uncharged compounds present in the reaction mixture will be soluble in the nonpolar liquid phase, while the charged compounds will be soluble in the polar phase. For instance, a polar phase may be an acidic or basic aqueous solution. After mixing of the two phases, the two liquids are separated by standard procedures, such as use of a separation funnel or centrifugation/aspiration. Where the desired product is not soluble in the added solution, for instance, an aqueous solution of 10% HCl, the extraction may be referred to as a washing.

In some instances, solid/liquid extractions can be used to purify desired products from unreacted reactants and by-products. In solid/liquid extractions a solid phase matrix containing charged or polar groups will bind to polar or oppositely charged compounds in the reaction mixture, while uncharged compounds or compounds having a charge of the same sign will not bind. Alternatively, if a hydrophobic resin is used in the extraction, uncharged, non-polar compounds will bind, while charged or polar compounds will not bind to the solid phase matrix.

A solid phase support is any macromolecular structure which is insoluble under the conditions for its use, and to which binding agents, reactants or catalysts can be attached, or which contains pores of a size to exclude desired product while permitting unreacted reactant to enter. The solid phase support may take different forms, have different physical characteristics, may be of different chemical compositions, and may be composed of a mixture of different chemical compositions, as long as the solid phase support is able to selectively retain unreacted reactants, desired product, or reactants or catalysts. The solid phase support should also be easily separated from the liquid phase, for instance, by trapping the solid phase support on the opposite side of a barrier containing openings of a size sufficient to completely block the flow of the solid support, while permitting the liquid phase and any soluble compounds in the liquid phase to readily pass through the openings. For example, the barrier may be a filter membrane.

Where binding agents, reactants or catalysts are attached to the solid phase support, the support may be porous, or non-porous. Where the solid phase support is used to remove unreacted reactant or to remove product, the degree of porosity will be chosen based on the binding capacity of the solid phase support, on the desired time for equilibration of interaction of the solid phase support with the reactant or product, and on the desired time for drainage and washing steps.

Preferably the removal or separation will take place in 1 hr. or less. In more preferred embodiments, the removal or separation will take place in 30 minutes or less, 15 minutes or less, or 5 minutes or less. In other preferred embodiments, the removal or separation will take place in 3 minutes or less, or 1 minute or less.

Several solid supports useful for separation of product from unreacted reactants have been described in the chemical and biochemical literature, and any such support may be used as long as the solid support is insoluble under the conditions used in the binding steps (including temperature, and solvent composition), and is substantially chemically inert to the binding conditions used.

In a third aspect, the invention relates to combinatorial libraries formed by carrying out the method described above using the template. A "combinatorial library" is a collection of compounds in which the compounds comprising the collection are composed of one or more types of subunits. The subunits may be selected from natural or unnatural moieties, including nucleophilic compounds, acylating agents, aromatic compounds, heterocyclic compounds, ethers, amines, carboxylic acids, amides, esters, thioesters, compounds containing a carbon-hetero multiple bond, L-amino acids, D-amino acids, synthetic amino acids, nucleotides, sugars, lipids, carbohydrates.

The compounds of the combinatorial library differ in one or more ways with respect to the number, order, type or types of, or modifications made to, one or more of the subunits comprising the compounds. Alternatively, a combinatorial library may refer to a collection or set of "core molecules" which vary as to the number, type or position of R or functional groups they contain and/or identity of molecules composing the core molecule. The collection of compounds is generated in a systematic way. Any method of systematically generating a collection of subunits differing from each other in one or more of the ways set forth above is a combinatorial library.

A template is thus useful for systematically synthesizing a large number of molecules that may vary greatly in their chemical structure or composition, or that may vary in minor aspects of their chemical structure or composition. The template is also useful for rapidly generating and developing large numbers of drug candidate molecules, and for developing new compounds useful in medicine, agriculture or basic research. The invention is therefore useful in randomly generating a large number of drug candidates, and later optimizing those candidates that show the most interesting biological behavior.

The templates and methods can be easily adapted for use in automated chemical synthesis of libraries of molecules with diverse structures. One such device is described in Brenner, U.S. patent application Ser. No. 08/281,194 filed Jul. 26, 1994, hereby incorporated by reference.

The combinatorial libraries generated by the methods of the present invention may be screened for pharmacologically active compounds, including peptide analogs. By pharmacologically active is meant that a compound may affect the functioning of a physiological process, such as signal transduction by a cellular receptor, initiation, cessation or modulation of an immune response, modulation of heart function, nervous system function, or any other organ or organ system. A pharmacologically active compound may also inhibit an endogenous enzyme involved in a pathogenic process, or block a binding interaction involved in a pathological process, such as a DNA/protein interaction or a protein/protein interaction. In addition, a pharmacologically active compound may stimulate or inhibit the activity of a bacteria, virus, fungus, or other infectious agent. A pharmacologically active compound may also modulate the effects of a disease, that is, to prevent or decrease the severity of, or cure a disease such as cancer, diabetes, atherosclerosis, high blood pressure, Parkinson's disease and other disease states. Screening for pharmacological activity may be performed as would be known in the art.

Compounds which have been shown to be pharmacologically active compounds may be formulated for therapeutic administration as described in detail below.

The combinatorial libraries generated by the methods of the present invention may also be screened for diagnostically useful compounds. By diagnostically useful is meant that the compound can be used to indicate the presence of a particular disease in a human or animal.

Still another aspect of this invention is a method of generating a template for combinatorial synthesis including the step of treating an iminodiacetic acid having a protected amine group with EDCI in situ to form a protected iminodiacetic acid anhydride. The amine group may be protected, for example with BOC. In addition, preferably the protected iminodiacetic acid will be treated with 1 equivalent of EDCI.

The templates of this invention are particularly useful in facilitating the separation of unreacted reactants or catalysts from the desired product in liquid phase chemical reactions. The methods of this invention utilize a template to synthesize functionalized products which are easily separated from unreacted reactants in a liquid phase or in solid phase/liquid phase extractions.

There are many advantages to use of a template in solution phase synthesis. For instance, use of the template permits separation of the unreacted reactants and desired products by means of a simple extraction procedure. Therefore, use of the template permits the ease of purification found in solid phase synthesis but eliminates the requirement for a covalent bond between a reactant and either an insoluble solid support or a soluble polymer support, which are required in solid phase synthesis or polymer-linked liquid phase synthesis, respectively. By eliminating this covalent bond and the need for the presence of a functionalization site to form the covalent bond with the solid support, use of the template permits purification of intermediates, and the use of a wider range of conditions than in solid phase synthesis or polymer-linked liquid phase synthesis. The template therefore permits the use of conditions, including reaction and washing solvents, reactants, protecting groups, and coupling methods which might cleave such a covalent bond. These advantages also facilitate the automation of combinatorial libraries.

Other advantages result from carrying out the reactions in a solution, in the absence of a large polymer. For instance, because synthesis using the template does not require attachment of a first reactant to a large polymer during the chemical reaction, there will be less steric hindrance during the reaction. In addition, reaction in a homogeneous solution can give rise to broader range of products compared with methods of solid phase synthesis.

Still another advantage of the template is the ease of scaling up a reaction which takes place in a homogeneous liquid phase.

Use of the template also facilitates separation of the desired product from failure products which failed to react at critical steps of the synthesis. In syntheses employing the template, chemical reactions occur in solution, yet unreacted reactants are easily separated from products by use of liquid/liquid phase extractions or liquid/solid phase extractions.

In addition, when the product is in the liquid phase, the completeness of the reaction can be monitored by taking aliquot volumes and analyzing the aliquots, e.g., by nuclear magnetic resonance, or by non-destructive spectrophotometric methods.

Furthermore, use of the template eliminates the potential need to introduce a functional group onto the reactant in order to form a reaction-insensitive linker to a solid support or soluble polymer.

Other and further objects, features and advantages will be apparent from the following description of the presently preferred embodiments of the invention.

BRIEF DESCRIPTION OF THE DRAWINGS

FIG. 4A illustrates the compound N'-((tert-Butyloxy)carbonyl)-N-benzyliminodiacetic Acid Monoamide.

FIG. 4B illustrates the compound N'-((tert-Butyloxy)carbonyl)-N-(n-butyl) iminodiacetic Acid Monoamide.

FIG. 4C illustrates the compound N'-((tert-Butyloxy)carbonyl)-N-cyclohexyliminodiacetic Acid Monoamide.

FIG. 5A illustrates the compound N'-(tert-Butyloxy)carbonyl)-N-(4-sec-butylphenyl)-N-cyclohexyliminodiacetic Acid Diamide.

FIG. 5B illustrates the compound N'-((tert-Butyloxy)carbonyl)-N-cyclohexyl-N-(3-methoxypropyl) iminodiacetic Acid Diamide.

FIG. 5C illustrates the compound N'-((tert-Butyloxy)carbonyl)-N-cyclohexyl-N-(2, 2-diphenylethyl) iminodiacetic Acid Diamide.

FIG. 5D illustrates the compound N'-((tert-Butyloxy)carbonyl)-N-benzyl-N-(4-sec-butylphenyl)iminodiacetic Acid Diamide.

FIG. 5E illustrates the compound N'-((tert-Butyloxy)carbonyl)-N-benzyl-N-(3-methoxypropyl) iminodiacetic Acid Diamide.

FIG. 5F illustrates the compound N'-((tert-Butyloxy)carbonyl)-N-benzyl-N-(2,2-diphenylethyl)iminodiacetic Acid Diamide.

FIG. 5G illustrates the compound N'-((tert-Butyloxy)carbonyl)-N-(n-butyl)-N-(4-sec-butylphenyl) iminodiacetic Acid Diamide.

FIG. 5H illustrates the compound N'-((tert-Butyloxy)carbonyl)-N-(n-butyl)-N-(3-methoxypropyl)iminodiacetic Acid Diamide.

FIG. 5I illustrates the compound N'-((tert-Butyloxy)carbonyl)-N-(n-butyl)-N-(2,2-diphenylethyl)iminodiacetic Acid Diamide.

FIG. 6A illustrates the compound N'-Benzylcarbonyl-N-cyclohexyl-N-(2,2-diphenylethyl)iminodiacetic Acid Diamide.

FIG. 6AA illustrates the compound N'-Ethylcarbonyl-N-(n-butyl)-N-(3-methoxypropyl)iminodiacetic Acid Diamide.

FIG. 7 depicts additional reaction products which have been generated by reaction scheme shown in FIG. 3

DETAILED DESCRIPTION OF THE INVENTION

This invention relates to compounds and methods for the chemical synthesis of organic compounds.

In one preferred embodiment, this invention describes a template having a plurality of functionalization sites. Preferably the template contains three sites which can be controllably functionalized with nucleophiles, acylating agents or electrophiles, enabling the synthesis of libraries with at least three variable regions.

In some preferred embodiments, the template may have a structure which imposes structural or conformational bias. In other preferred embodiments, the template may be symmetrical so that the template imposes little structural or conformational bias.

Preferably two of the functionalization sites on the template are blocked by a protecting group during the first reaction to form the first modified template, in order to insure that the only one of the functionalization sites is functionalized during a reaction step. A protecting group is any chemical group covalently bonded to a protected functionalization site group which prevents the functionalization site group from participating in the chemical reactions used to modify other functionalization sites. Protecting groups may include protecting groups traditionally used in the synthesis of peptides or oligonucleotides, such as t-butoxycarbonyl (BOC), or 9-fluorenylmethoxycarbonyl (Fmoc). In addition, protecting groups may include a group within the same molecule to which the protected functionalization site group is covalently bonded, e.g., the activated acyl group in an anhydride acts as a protecting group for the other acyl group in an anhydride. The reaction should tolerate any number of protecting groups on nitrogen, as would be known to one of ordinary skill in the art, for example, BOC or Fmoc. More generally, any protecting group which does not interfere with reaction of the unprotected functionalization sites of the template may be utilized.

A protecting group may either detached from the functionalization site group during the reaction of an unprotected functionalization site group, or the protecting group may be removed in a separate reaction prior to modification of the protected functionalization site group.

Figure 1:
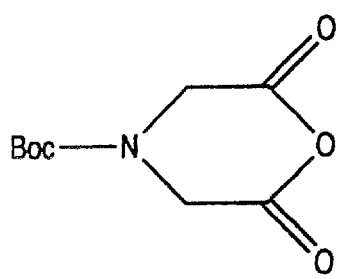
FIG. 1 illustrates one generic structure for a template. The template in FIG. 1 is representative of a series of anhydride-based templates.

One preferred embodiment of a template is derived from the generic template structure illustrated in FIG. 1. In a particularly preferred embodiment, the template will be N-((tert-butyloxy)carbonyl)iminodiacetic acid. The template shown in FIG. 1 is flexible, possessing 1–3 functionalizable sites for diversification and little inherent structural or conformational bias which might limit its use. The functionalizable sites are carboxylic acid groups, derivatives of carboxylic acid groups, or an amine. In the preferred embodiment shown, one of the functionalizable groups is a secondary amine protected by a butoxycarbonyl (BOC) group. The two other functionalizable sites groups are carboxylic acid groups converted to an anhydride, for example, by treatment in situ with 1-ethyl-3-(3-dimethylaminopropyl) carbodiimide) (EDCI).

Another preferred embodiment of this invention is a method of generating a template for combinatorial synthesis including the step of treating an iminodiacetic acid having a protected amine group with EDCI in situ to form a protected iminodiacetic acid anhydride. A method of generating the template in FIG. 1 from N-BOC-iminodiacetic acid is described below in Example 1.

In another preferred embodiment, this invention features a method of liquid phase combinatorial synthesis utilizing a template having two or more functionalization sites, including the following steps:

(a) reacting one functionalization site of the template with at least one reactant;

(b) repeating step (a) at least once.

Figure 2:
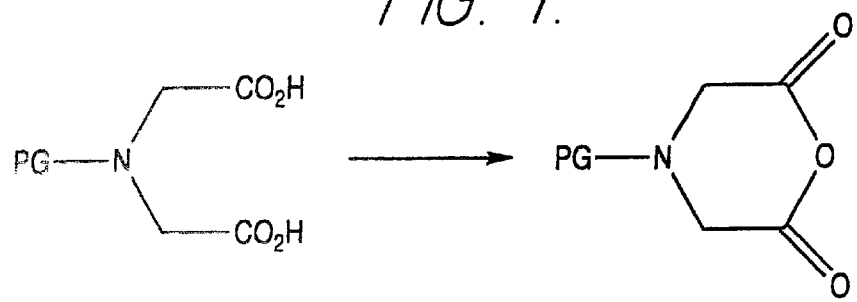
FIG. 2 depicts a generic reaction scheme in which the anhydride template illustrated in FIG. 1 is generated in situ from a dicarboxylic acid, and reacted with three reactants in a three step reaction procedure.
Figure 2:
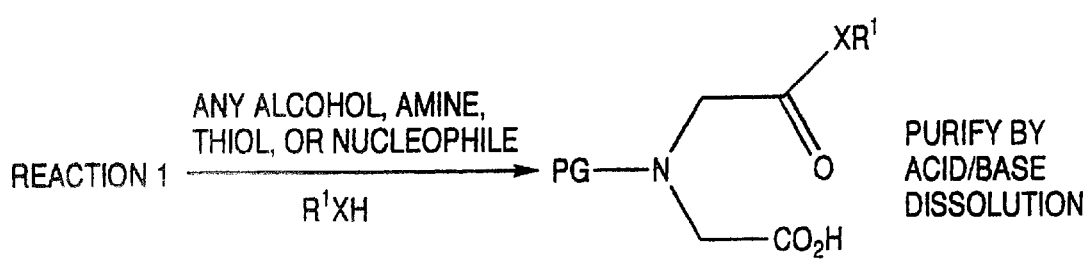
Figure 2:
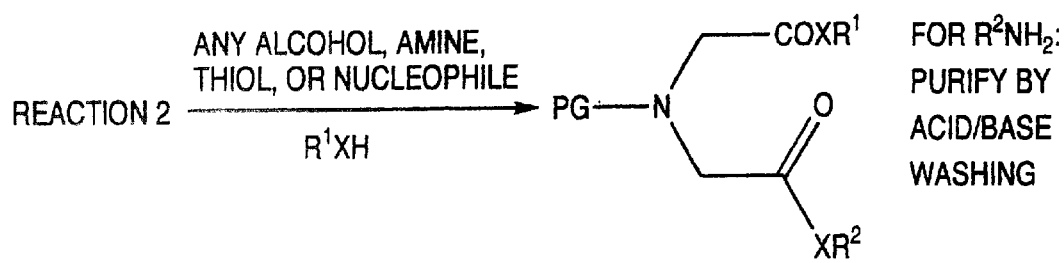
Figure 2:
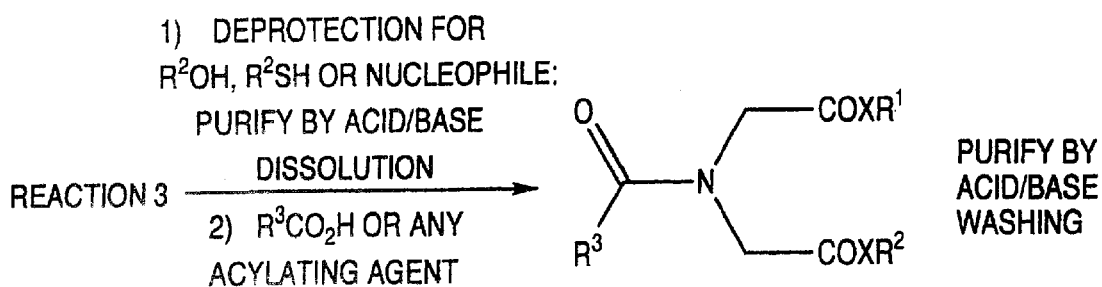
Figure 3:
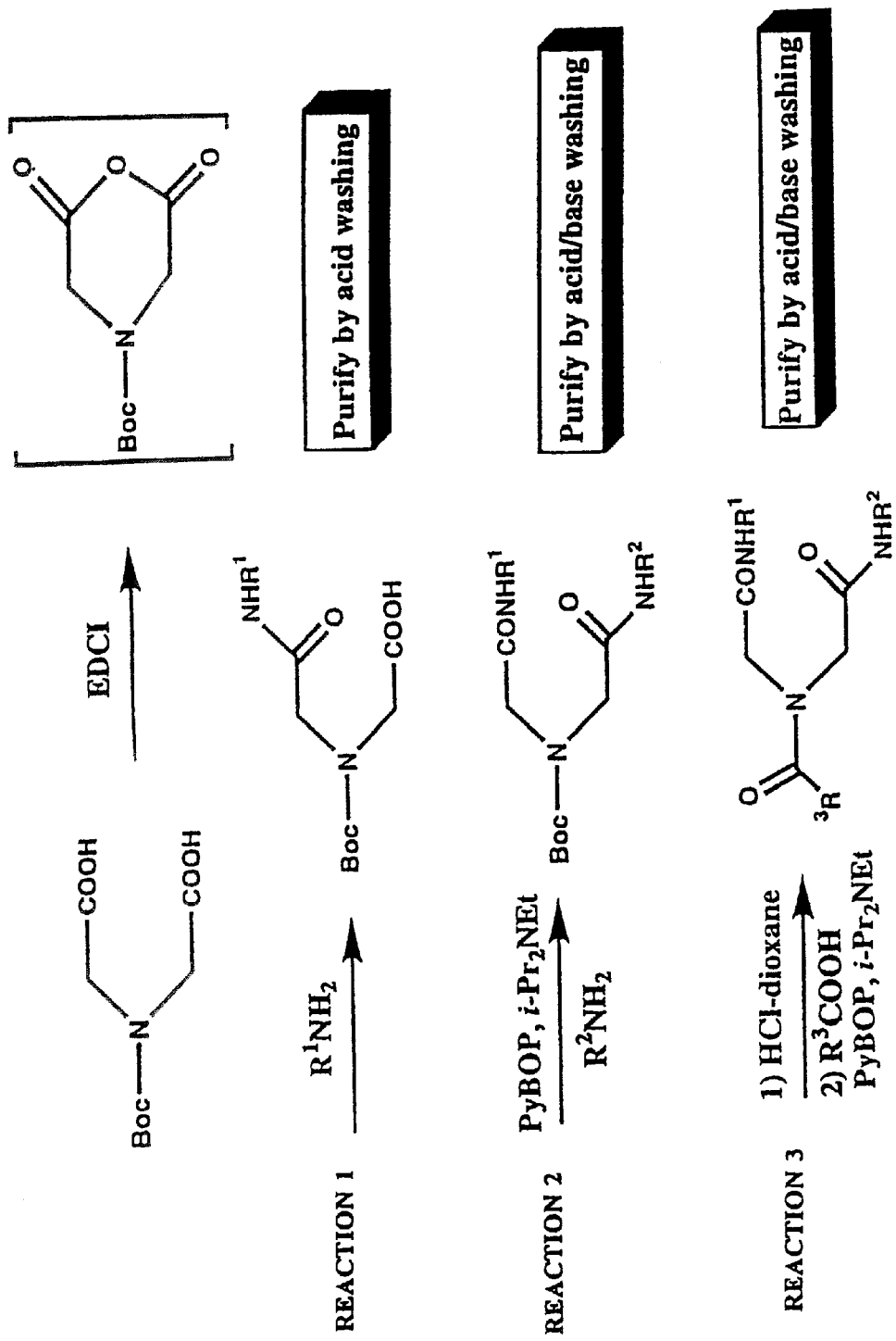
FIG. 3 shows a reaction scheme in which some of the generic groups in the scheme in FIG. 2 have been specified.
Figure 4A:
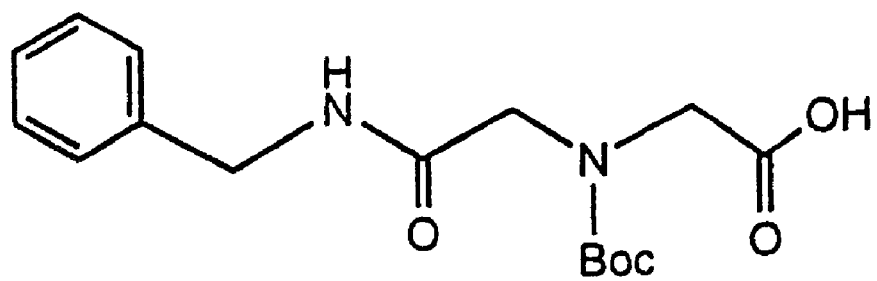
FIGS. 4A–C depict reaction products generated by Reaction 1 in the reaction scheme shown in FIG. 3 using reactants A1–3 shown in TABLE 1.
Figure 4B:
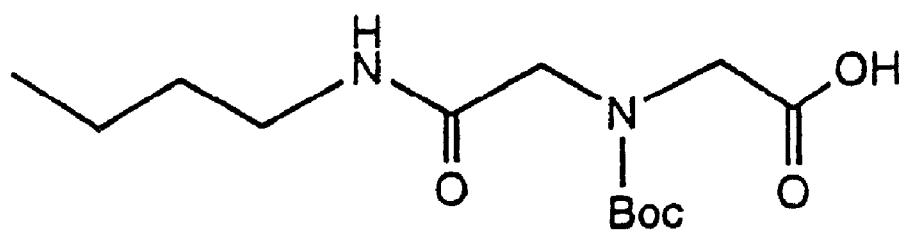
Figure 4C:
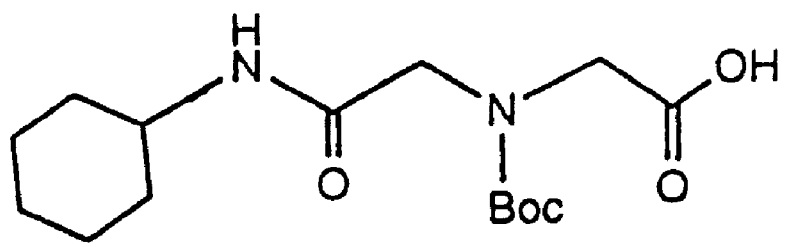
Figure 5A:
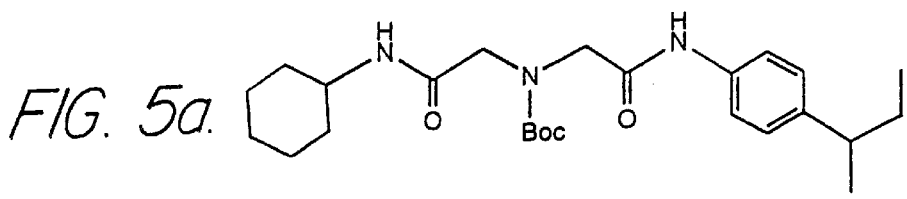
FIGS. 5A–I show the reaction products generated by Reaction 2 in the reaction scheme shown in FIG. 3 in which the products of Reaction 1 shown in FIGS. 4A–C have been reacted with reactants B1–3 shown in TABLE 2.
Figure 5B:
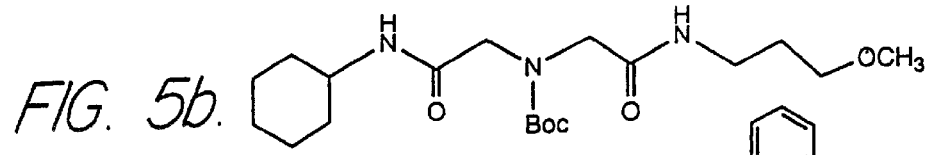
Figure 5C:
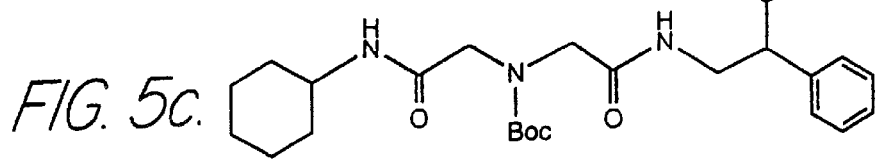
Figure 5D:
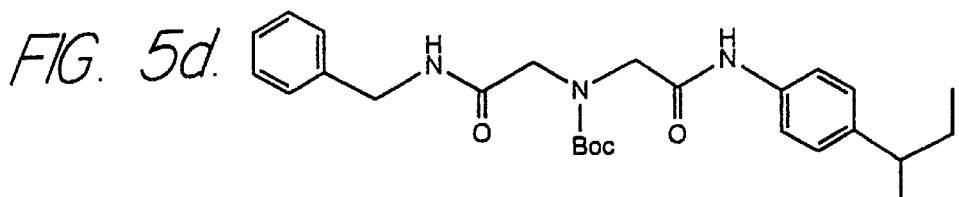
Figure 5E:
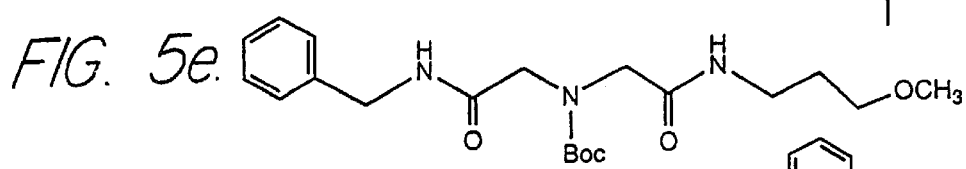
Figure 5F:
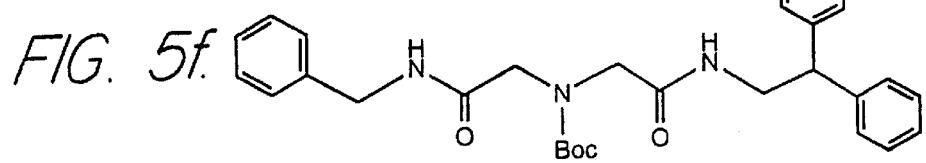
Figure 5G:
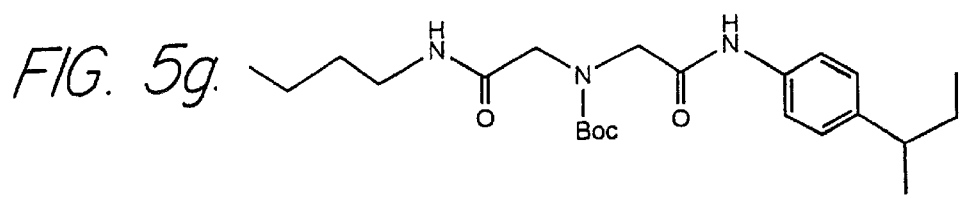
Figure 5H:
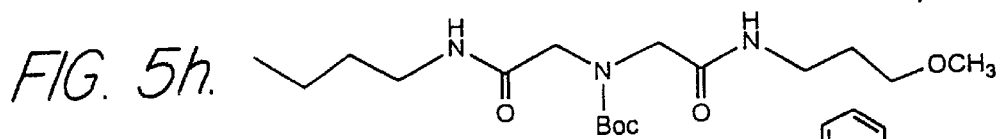
Figure 5I:
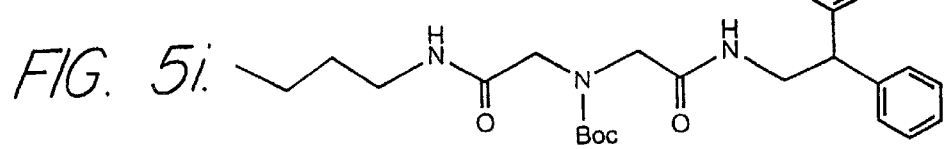
Figure 6A:
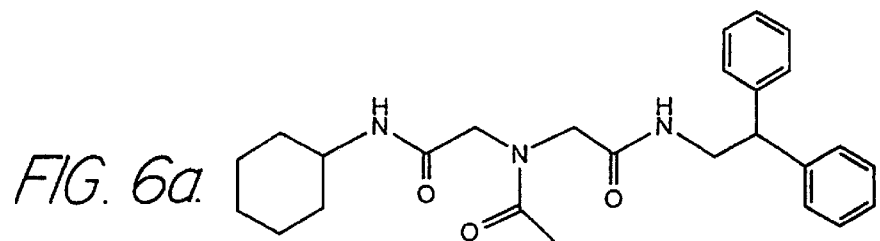
FIGS. 6A–AA show the reaction products generated by Reaction 3 in the reaction scheme shown in FIG. 3 in which the products of Reaction 2 shown in FIGS. 5A–I have been reacted with reactants C1–3 in TABLE 3.
Figure 6B:
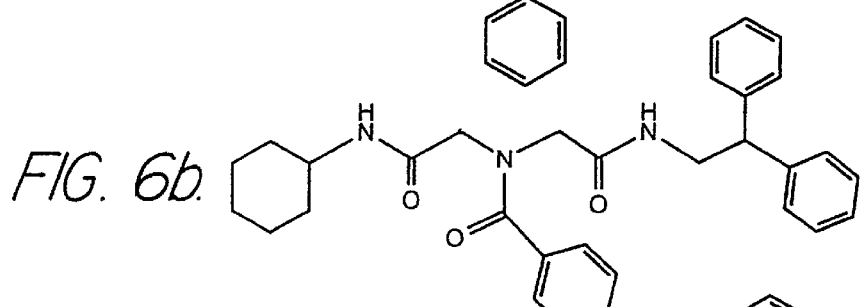
FIG. 6B illustrates the compound N'-Benzoyl-N-cyclohexyl-N-(2,2-diphenylethyl) iminodiacetic Acid Diamide.
Figure 6C:
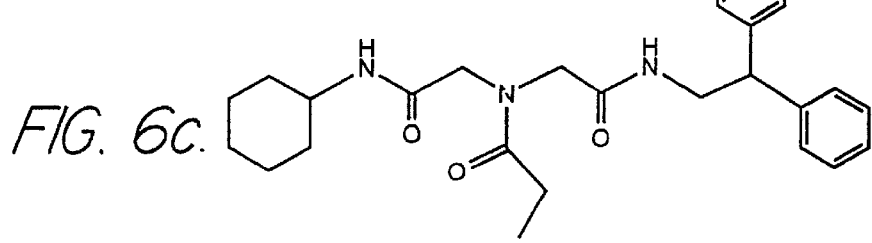
FIG. 6C illustrates the compound N'-Ethylcarbonyl-N-cyclohexyl-N-(2,2-diphenylethyl) iminodiacetic Acid Diamide.
Figure 6D:
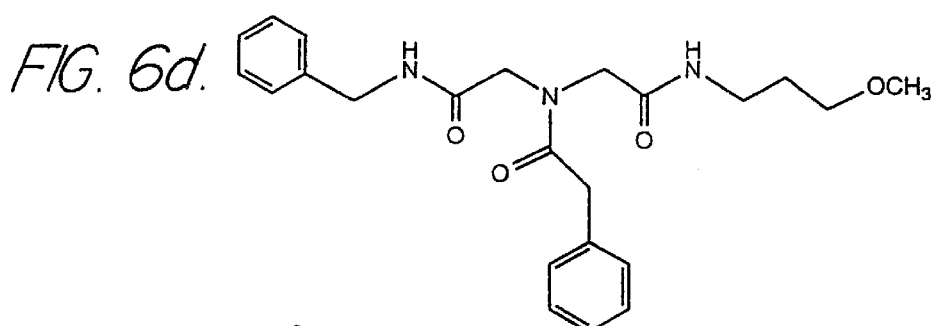
FIG. 6D illustrates the compound N'-Benzylcarbonyl-N-benzyl-N-(3-methoxypropyl) iminodiacetic Acid Diamide.
Figure 6E:
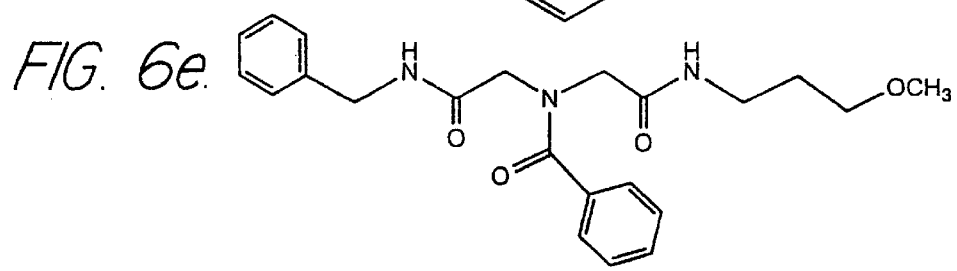
FIG. 6E illustrates the compound N'-Benzoyl-N-benzyl-N-(3-methoxypropyl)iminodiacetic Acid Diamide.
Figure 6F:
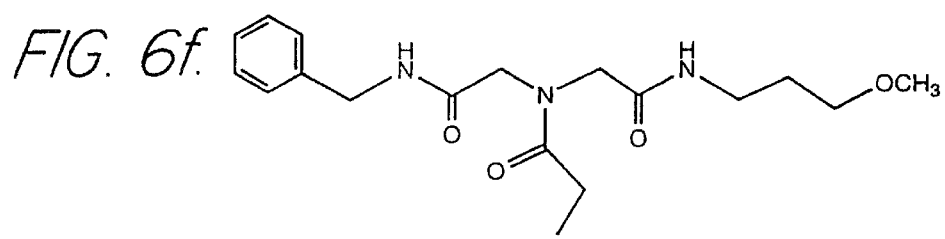
FIG. 6F illustrates the compound N'-Ethylcarbonyl-N-benzyl-N-(3-methoxypropyl) iminodiacetic Acid Diamide.
Figure 6G:
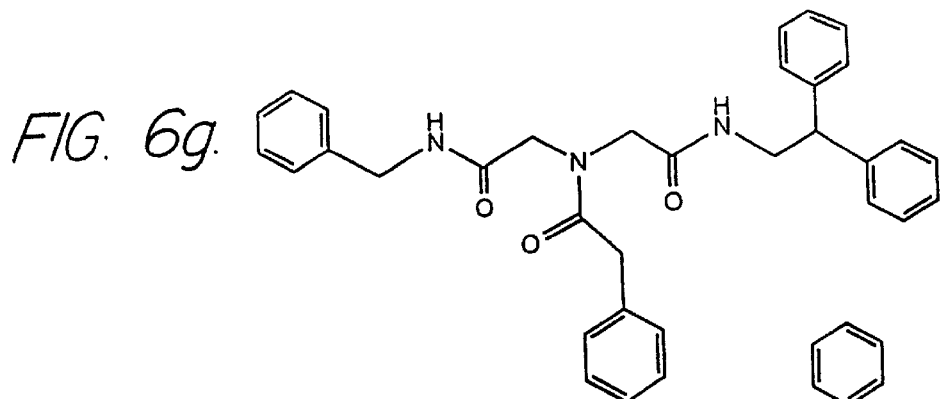
FIG. 6G illustrates the compound N'-Benzylcarbonyl-N-benzyl-N-(2,2-diphenylethyl) iminodiacetic Acid Diamide.
Figure 6H:
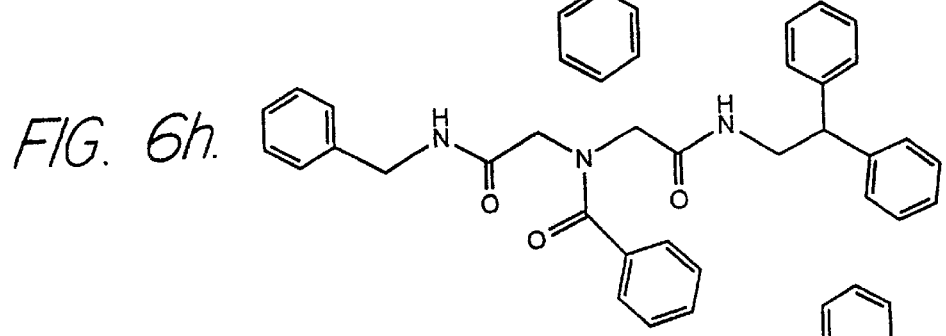
FIG. 6H illustrates the compound N'-Benzoyl-N-benzyl-N-(2,2-diphenylethyl)iminodiacetic Acid Diamide.
Figure 6I:
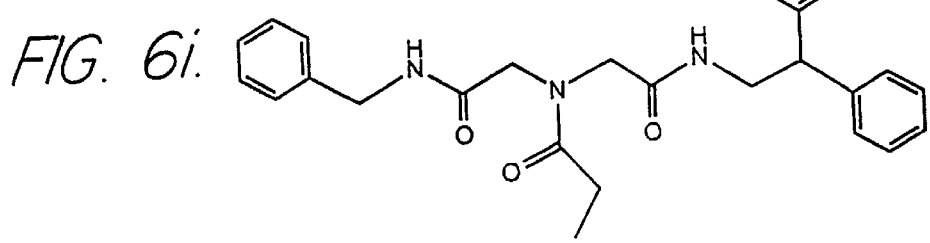
FIG. 6I illustrates the compound N'-Ethylcarbonyl-N-benzyl-N-(2,2-diphenylethyl) iminodiacetic Acid Diamide.
Figure 6J:
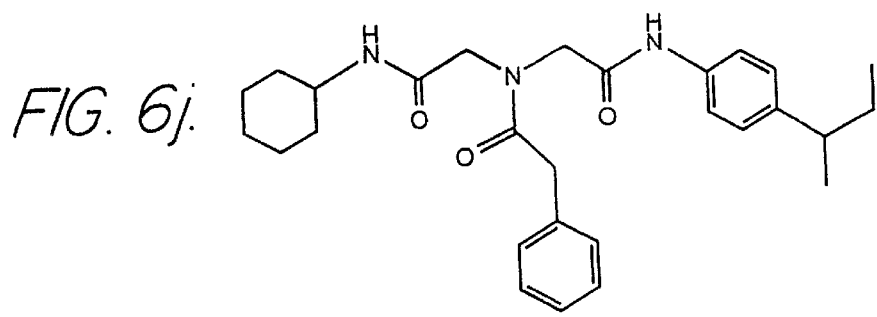
FIG. 6J illustrates the compound N'-Benzylcarbonyl-N-(4-sec-butylphenyl)-N-cyclohexyliminodiacetic Acid Diamide.
Figure 6K:
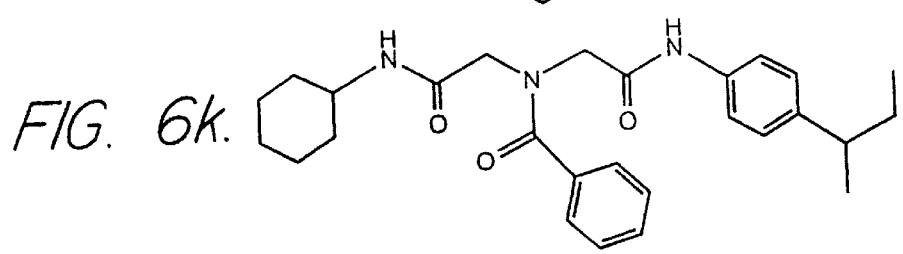
FIG. 6K illustrates the compound N'-Benzoyl-N-(4-sec-butylphenyl)-N-cyclohexyliminodiacetic Acid Diamide.
Figure 6L:
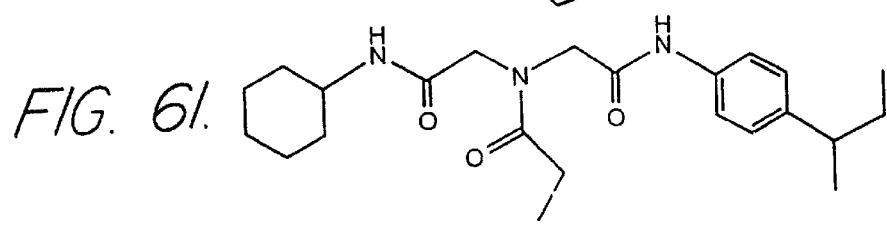
FIG. 6L illustrates the compound N'-Ethylcarbonyl-N-(4-sec-butylphenyl)-N-cyclohexyliminodiacetic Acid Diamide.
Figure 6M:
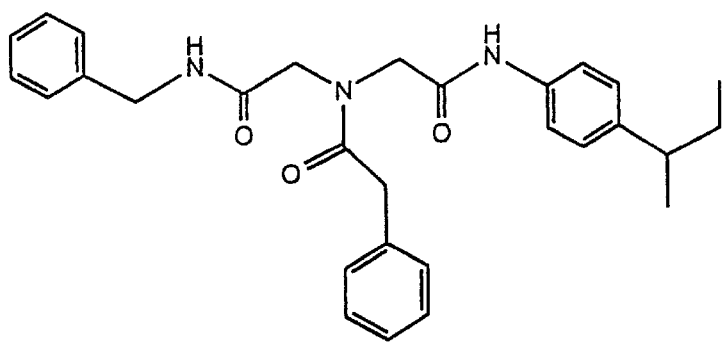
FIG. 6M illustrates the compound N'-Benzylcarbonyl-N-benzyl-N-(4-sec-butylphenyl) iminodiacetic Acid Diamide.
Figure 6N:
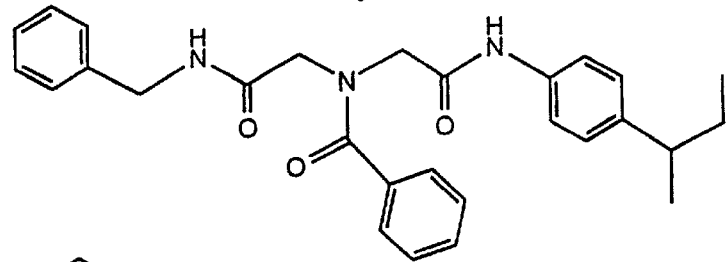
FIG. 6N illustrates the compound N'-Benzoyl-N-benzyl-N-(4-sec-butylphenyl)iminodiacetic Acid Diamide. sec-butylphenyl)iminodiacetic Acid Diamide.
Figure 6O:
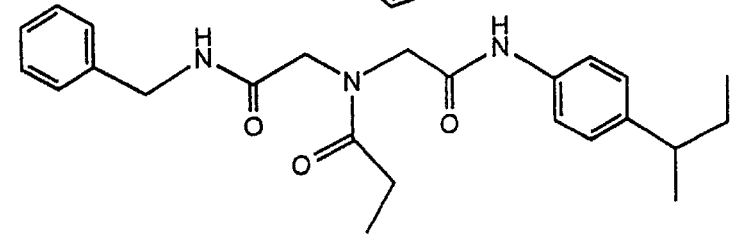
FIG. 6O illustrates the compound N'-Ethylcarbonyl-N-benzyl-N-(4-sec-butylphenyl) iminodiacetic Acid Diamide.
Figure 6P:
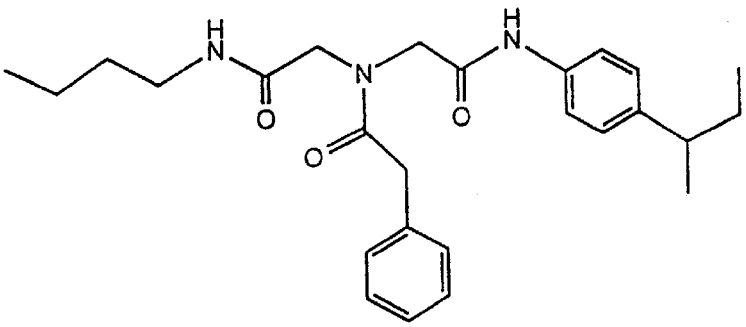
FIG. 6P illustrates the compound N'-Benzylcarbonyl-N-(n-butyl)-N-(4-sec-butylphenyl)iminodiacetic Acid Diamide.
Figure 6Q:
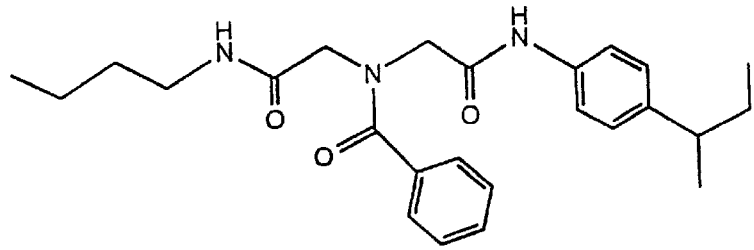
FIG. 6Q illustrates the compound N'-Benzoyl-N-(n-butyl)-N-(4-sec-butylphenyl) iminodiacetic Acid Diamide.
Figure 6R:
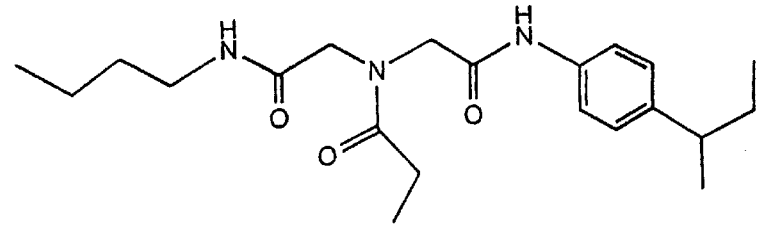
FIG. 6R illustrates the compound N'-Ethylcarbonyl-N-(n-butyl)-N-(4-sec-butylphenyl)iminodiacetic Acid Diamide.
Figure 6S:
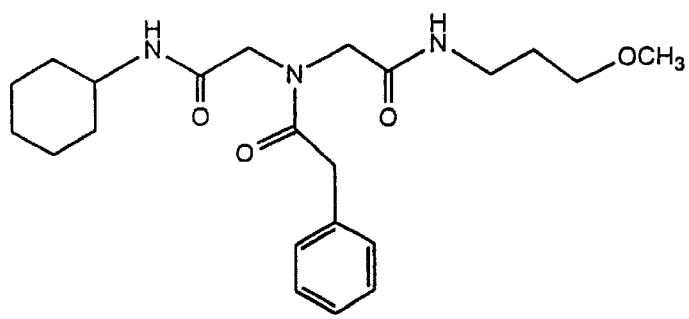
FIG. 6S illustrates the compound N'-Benzylcarbonyl-N-cyclohexyl-N-(3-methoxypropyl)iminodiacetic Acid Diamide.
Figure 6T:
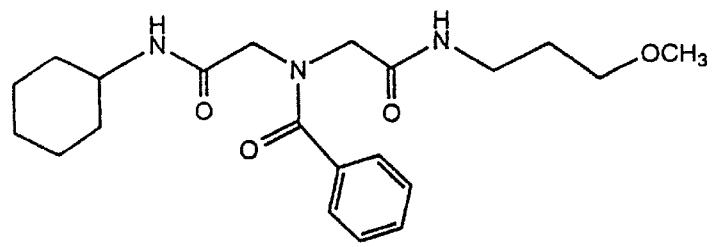
FIG. 6T illustrates the compound N'-Benzoyl-N-cyclohexyl-N-(3-methoxypropyl) iminodiacetic Acid Diamide.
Figure 6U:
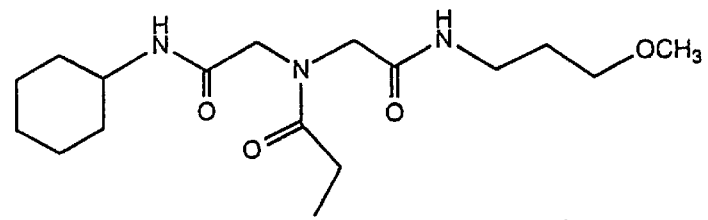
FIG. 6U illustrates the compound N'-Ethylcarbonyl-N-cyclohexyl-N-(3-methoxypropyl) iminodiacetic Acid Diamide.
Figure 6V:
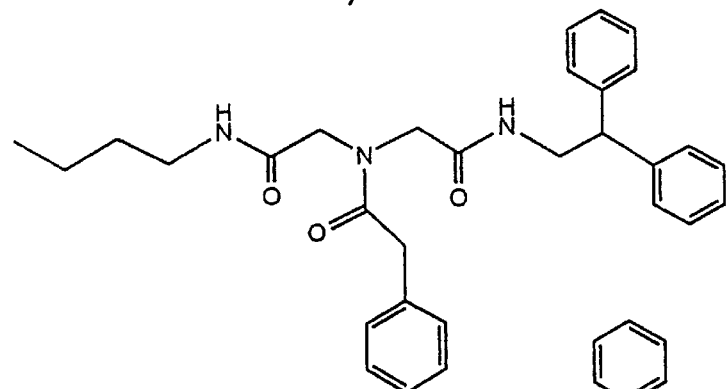
FIG. 6V illustrates the compound N'-Benzylcarbonyl-N-(n-butyl)-N-(2,2-diphenylethyl)iminodiacetic Acid Diamide.
Figure 6W:
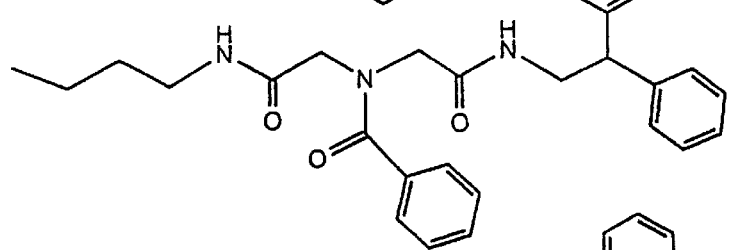
FIG. 6W illustrates the compound N'-Benzoyl-N-(n-butyl)-N-(2,2-diphenylethyl) iminodiacetic Acid Diamide.
Figure 6X:
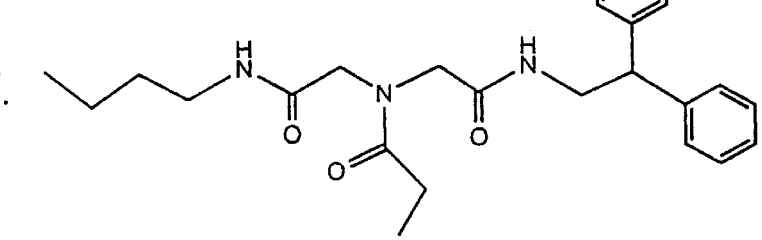
FIG. 6X illustrates the compound N'-Ethylcarbonyl-N-(n-butyl)-N-(2,2-diphenylethyl)iminodiacetic Acid Diamide.
Figure 6Y:
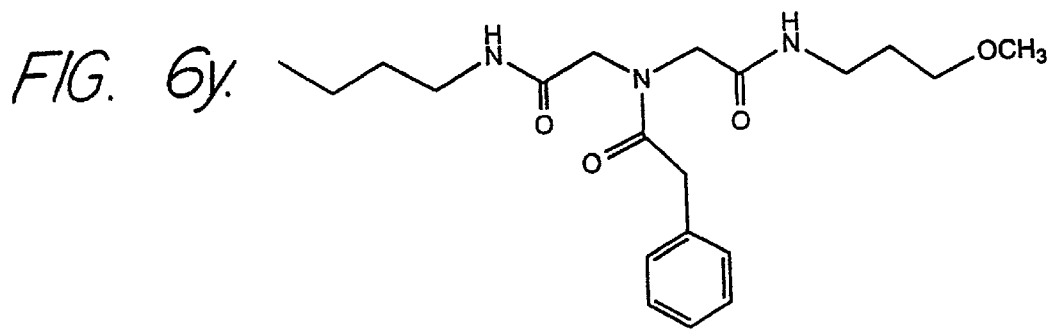
FIG. 6Y illustrates the compound N'-Benzylcarbonyl-N-(n-butyl)-N-(3-methoxypropyl)iminodiacetic acid Diamide.
Figure 6Z:
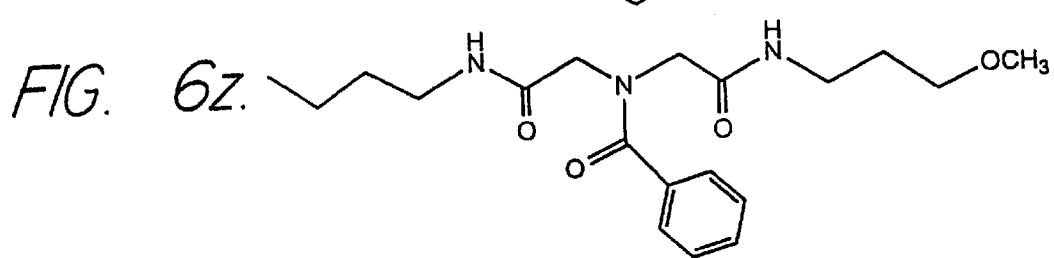
FIG. 6Z illustrates the compound N'-Benzoyl-N-(n-butyl)-N-(3-methoxypropyl) iminodiacetic Acid Diamide.
Figure 6A:
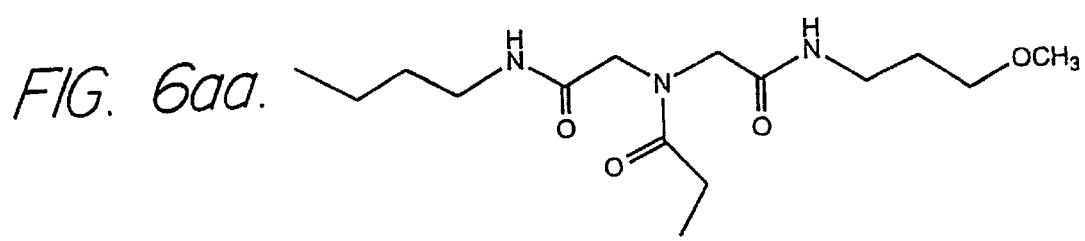
Figure 7A:
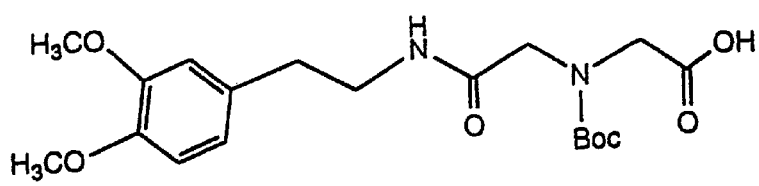
FIG. 7A illustrates the compound N'-((tert-Butyloxy)carbonyl)-N-(3,4-dimethoxyphenethyl)iminodiacetic acid monoamide.
Figure 7B:
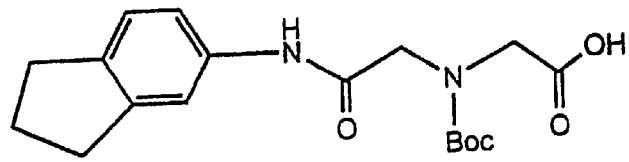
FIG. 7B illustrates the compound N'-((tert-Butyloxy)carbonyl)-N-(5-indan)iminodiacetic acid monoamide.
Figure 7C:
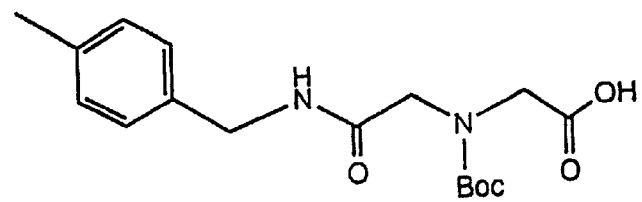
FIG. 7C illustrates the compound N'-((tert-Butyloxy)carbonyl)-N-(4-methylbenzyl) iminodiacetic acid monoamide.
Figure 7D:
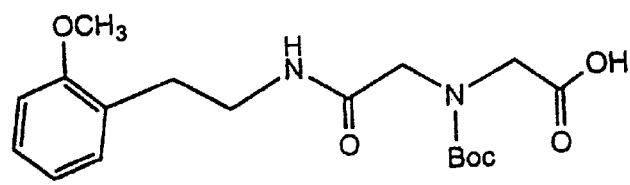
FIG. 7D illustrates the compound N'-((tert-Butyloxy)carbonyl)-N-(2-methyoxyphenethyl) iminodiacetic acid monoamide.
Figure 7E:
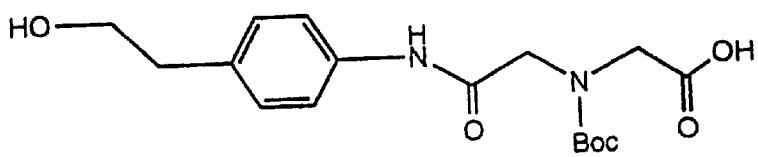
FIG. 7E illustrates the compound N'-((tert-Butyloxy)carbonyl)-N-(4-ethanolphenyl)iminodiacetic acid monoamide.
Figure 7F:
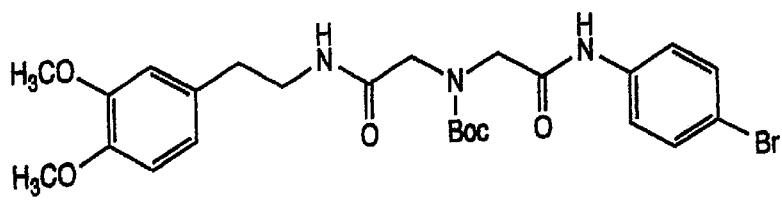
FIG. 7F illustrates the compound N'-((tert-Butyloxy)carbonyl)-N-(3,4-dimethoxyphenethyl)-N-(4-bromophenyl) iminodiacetic acid diamide.
Figure 7G:
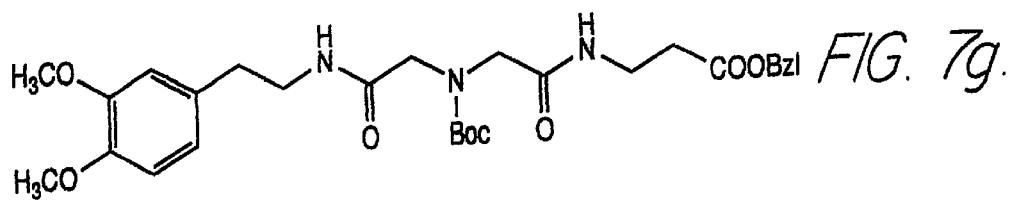
FIG. 7G illustrates the compound N'-((tert-Butyloxy)carbonyl)-N-(2-benzylcarboxylate-ethyl)- N-(3,4-dimethoxyphenethyl)iminodiacetic acid diamide.
Figure 7H:
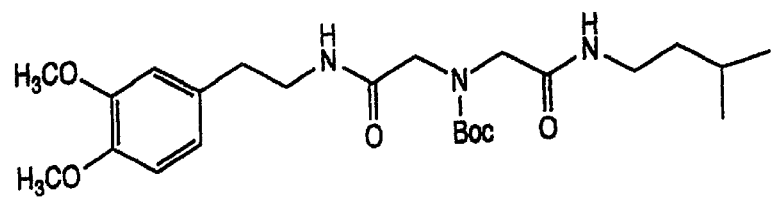
FIG. 7H illustrates the compound N'-((tert-Butyloxy)carbonyl)-N-(3,4-dimethoxyphenethyl)-N-(isoamyl) iminodiacetic acid diamide.
Figure 7I:
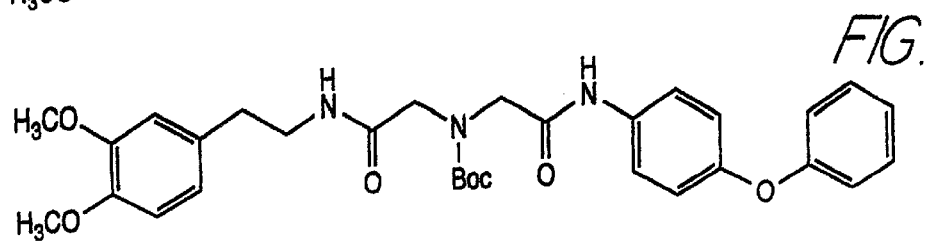
FIG. 7I illustrates the compound N'-((tert-Butyloxy)carbonyl)-N-(3,4-dimethoxyphenethyl)-N-(4-phenoxyphenyl)iminodiacetic acid diamide.
Figure 7J:
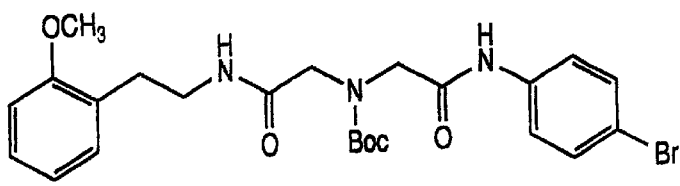
FIG. 7J illustrates the compound N'-((tert-Butyloxy)carbonyl)-N-(4-bromophenyl)-N-(2-methoxyphenethyl) iminodiacetic acid diamide.
Figure 7K:
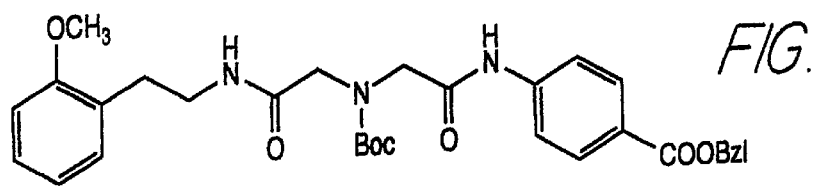
FIG. 7K illustrates the compound N'-((tert-Butyloxy)carbonyl)-N-(2-benzylcarboxylate-ethyl)- N-(2-methoxyphenethyl)iminodiacetic acid diamide

For example, in a first set of reactions, separate aliquots of reaction mixture containing the template are individually reacted with one of first reactants $A_2 \ldots A_n$ to yield a set of first modified products, each containing a functional group at the first functionalization site, which can be the same or different. A preferred reaction scheme using a preferred embodiment of the template is shown in FIG. 2. An even more preferred reaction scheme is shown in FIG. 3. Preferred embodiments of first modified products are shown in FIG. 4. In some instances, two or more aliquots of the template may be reacted with the same first reactant. However, if each first reactant reacted with each aliquot of template is unique, the number of first modified products is equal to the number of first reactants.

Next, each of the first modified products is divided into aliquots and reacted with one of a series of second reactants $B_2 \ldots B_n$ to yield a set of second modified products containing all possible combinations of first functional groups and second functional groups, i.e., $A_1B_1$, $A_1B_2$, $A_1B_3 \ldots A_nB_n$. Preferred embodiments of second modified products are shown in FIG. 5. In some instances, two or more in the series of second reactants will be the same. However, if each of the first reactants is unique and each of the second reactants is different from the other second reactants, the number of second modified products will be the number of first reactants multiplied times the number of second reactants.

Each of the second modified products can then be divided into aliquots and reacted with one of third reactants $C_1 \ldots C_n$ to yield a set of third modified products. Preferred embodiments of third modified products are shown in FIG. 6 and FIG. 7. FIG. 6 also represents the compounds in a preferred embodiment of a combinatorial library of compounds synthesized using the preferred embodiment of a template.

If each of the first reactants is different from each of the other first reactants, each of the second reactants is different from each of the other second reactants, and each of the third reactants is different from each of the other third reactants, the number of third modified products will be equal to the number of first reactants multiplied times the number of second reactants times the number of third reactants. For example, if the number of first reactants is 3, the number of second reactants is 3, and the number of third reactants is 3, the number of products in the combinatorial library will be 3×3×3=27. In addition, the library would be referred to as a 3×3×3 library. The size of the library can be increased by increasing the number of reactants at each reaction step.

Moreover, if the template contains additional functionalization sites or if one or more of the reactants contains additional functionalization sites, additional reaction steps can give rise to larger and larger combinatorial libraries.

In a preferred series of functionalization reactions carried out with the preferred embodiment of the template (a symmetrical molecule containing anhydride and protected secondary amine functionalization sites), the first reaction will be a nucleophilic substitution reaction of one acyl group of the anhydride functionalization site. The anhydride group in this embodiment of the template contains one acyl group which is susceptible to a nucleophilic substitution reaction. During the nucleophilic substitution, the nucleophile attacks one acyl group of the anhydride, displacing the second acyl group, which leaves as a carboxylic acid group. The reaction therefore simultaneously results in functionalization of the first acyl functionalization site and liberation of the second carboxylic acid functionalization site ($-CO_2H$). The nucleophile will preferably be an alcohol, amine, or thiol.

In a second reaction step, a second reactant, preferably an alcohol, amine, thiol or nucleophile is reacted with the free carboxylic acid to convert the carboxylic acid to, for example, an amide, ester, thioester, or other derivative of a carboxylic acid. For example, the carboxylic acid may be reacted with a primary amine in the presence of diisopropyl ethylamine and PyBOP to form an amide.

Following the second reaction step, the protecting group can be removed from the secondary amine, and the secondary amine can be reacted with, for example, a carboxylic acid in the presence of diisopropyl ethylamine and PyBOP to form an amide.

Thus, no orghogonal protecting groups are required for the template functionalization and only four chemical steps are required for the $N^3$ diversification of this embodiment of the template (FIG. 2).

TABLE 1 shows reactants which were used in synthesizing a 3×3×3 combinatorial library with the template.

TABLE 1

| $R^1NH_2$ | $R^2NH_2$ | $R^3COOH$ |
|---|---|---|
| 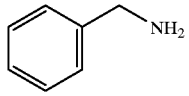 A1 | 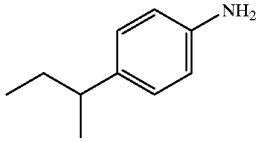 B1 | 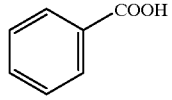 C1 |
| 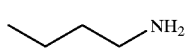 A2 | 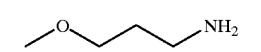 B2 | 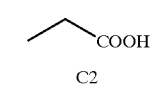 C2 |
| 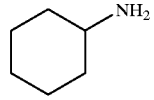 A3 | 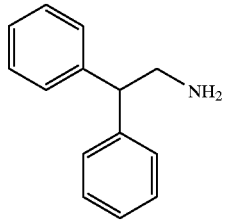 B3 | 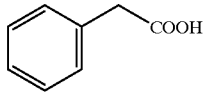 C3 |

TABLE 2 shows additional reactants which were used in synthesizing a combinatorial library. Use of these reactants generates a 5×5×5 combinatorial library.

reagents and their reaction by-products by simple liquid/liquid or solid/liquid extraction providing highly pure materials (≧90–95%) regardless of the reaction efficiencies.

TABLE 2

| R¹NH₂ | R²NH₂ | R³COOH |
|---|---|---|
| 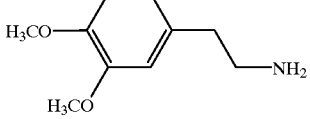 A1 |  B1 | 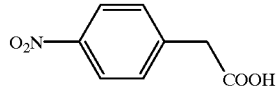 C1 |
| 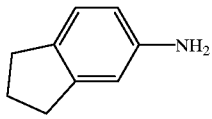 A2 | 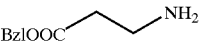 B2 | 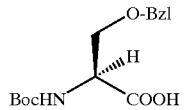 C2 |
| 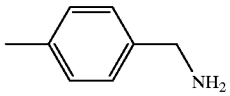 A3 | 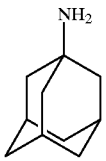 B3 | 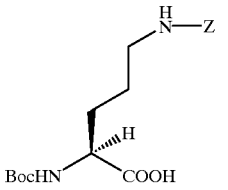 C3 |
| 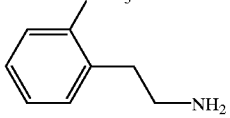 A4 | 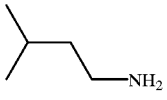 B4 | 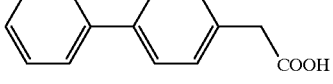 C4 |
| 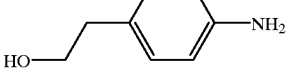 A5 | 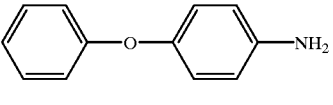 B5 | 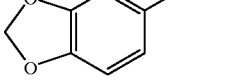 C5 |

In a still more preferred embodiment, the first reactants will be selected from the group of reactants A1 to A3, and B1 to B3, shown in Table 1, and A1 to A5, and B1 to B5, shown in Table 2. In this still more preferred embodiment, second reactants will be selected from the group of reactants A1 to A3, and B1 to B3, shown in Table 1, and A1 to A5, and B1 to B5, shown in Table 2. Moreover, in this embodiment, third reactants will be selected from the group of reactants C1 to C3 shown in Table 1 and C1 to C5 shown in Table 2.

In an even more preferred embodiment, the first reactants will be selected from reactants A1 to A3 in Table 1, the second reactants will be selected from reactants B1 to B3 shown in Table 1, and third reactants will be selected from reactants C1 to C3 shown in Table 1.

In addition, in a second even more preferred embodiment, the first reactants may be selected from reactants A1 to A5 in Table 2, the second reactants may be selected from reactants B1 to B5 in Table 2, and the third reactants may be selected from reactants C1 to C5 in Table 2.

At each step, the same liberated functionality may be used for both the isolation and purification of the intermediates and expected products from the starting material, reactants, In addition, the extraction conditions can be varied to alter the distribution of the desired products and unreacted reactants between the two phases. Conditions may be optimized to provide maximum separation of desired product from unreacted reactants. These changes may include, e.g., changes in the pH, hydrophobicity, ion concentration, temperature.

For example, where the reaction liberates a carboxylic acid, positively charged reagents such as EDCI and its byproducts can be removed by acidifying the reaction mixture by dissolving in 10% HCl. The positively charged compounds are soluble in the aqueous phase, while the carboxylic acid product, which is neutral at this pH, is soluble in the nonpolar reaction solvent phase. If the first reactant was a primary amine, unreacted first reactant will also be soluble in the acidified aqueous phase, and the acid extraction is sufficient to obtain purification of the desired product.

If the first reactant is a nucleophile which is neutral at an acid pH (e.g., $R^1OH$, $R^1SH$, or $R^1$-Met), following the acid washing, the carboxylic acid first modified template can then be separated from the unreacted neutral first reactant by extraction of the carboxylic acid into 10% aqueous NaOH.

The product can then be isolated by reacidification and extraction into ethanolacetate or $CH_2Cl_2$.

Following the reaction of the template with a second reactant, acid/base extractions can be used to purify the second modified template product from unreacted reactants or by-products. For example, where the second reactant is a neutral nucleophile, the further purification of the neutral reactants from the desired products can be readily accomplished upon N-BOC deprotection of the second-modified template to yield a secondary amine, and aqueous acid extraction of the resulting secondary amine. Where the second reactant is a primary amine, the desired product can be purified by acid/base washings, because the product containing the protected secondary amine will be neutral in both dilute aqueous acid and dilute aqueous base.

Following reaction with a third reactant, which is preferably a carboxylic acid, in some instances the product may be purified from positively charged reagents and from the negatively charged third reactant by acid/base washings.

Although the initial example described above enlists conventional liquid/liquid extractions, similar results employing solid-supported ion exchange resins, columns, or pads have been used to effect solid/liquid extractions by simple batch, column, or filtration protocols. In addition, the separation may be performed utilizing methods of inverse solid phase synthesis described in Caporale, L. H., U.S. Ser. No. 08/483,143.

The one secondary amine protecting group may be easily altered to accommodate its sensitivity to selected liquid/liquid or liquid/solid extraction protocols used to remove starting materials and reaction byproducts.

Solid phase supports appropriate for purifying some of the products from each reaction step may be commercially available from various sources, including Biorad, Pharmacia Fine Chemicals (Uppsala, Sweden; Piscataway, N.J.), Sigma Chemical Company (St. Louis, Mo.), 3M (St. Paul, Minn.). For example, if the excess reactant is an anion, an anion exchange resin can be used to bind the excess reactant. Examples of anion exchange resins include AG-1 and AG MP-1 resins, which bear the functional group $R—CH_2N^+(CH_3)_3$, AG-2 resins, which bear the functional group $R—CH_2(CH_2H_4OH)N^+(CH_3)_3$ and AG-4 resins, which bear the functional group $R—CH_2N^+H(CH_3)_2$ on an acrylic matrix, AG-3 resins, which bear the functional group $R—CH_2N+H(CH_3)_2$, BioRex 5 resin, which bears the functional groups $R—N^+H(CH_3)_3$ and $R—N^+(CH_3)_2C_2H_4OH$, resins which bear the functional group diethylaminoethyl (DEAE), and resins which bear the quaternary ammonium group $N^+(CH_3)_3(Q)$. Still another example is the Empore™ extraction disk containing a quaternary ammonium functional group.

An excess reactant which is a cation can be bound and removed by the use of a cation exchange resin. Examples of cation exchange resins include S, AG50W and AG-MP 50 resins, bearing the functional group $R—SO_3^-$, and Bio Rex 70 and CM resins, which bear the functional group $R—COO^-$, the Empore™ cation exchange disk (containing a sulfonic acid functional group), and chelating resins which can remove polyvalent cations with high selectivity. An example of a chelating resin is Chelex 100, which contains the functional group $R—CH_2N(CH_2COO^-)_2$.

If it is desired to remove both cations and anions from the neutral product of a reaction (e.g., "desalt" a product), a resin containing both anionic and cationic functional groups can be used. Examples of such resins include mixed bed type resins such as AG501-X8 and Bio-Rex MSZ 501 type resins, which contain both $R—SO_3^-$, and $R—CH_2N^+(CH_3)_3$ groups. A resin bearing weaker cations and anions, such as the "ion retardation" resin AG11A8 can be used to "desalt" even products containing anions and cations due to the differential affinity of salts and weaker anions to such a resin, as is used by one skilled in the art.

Other materials, commonly used in chromatography, can be introduced into the reaction vessel in order to separate product from excess reactants. For example, conditions can be adjusted by one skilled in the art so that a resin used in reverse phase chromatography can bind product or reactant to separate product from excess reactant. In addition, adjustment of the conditions by those skilled in the art can allow selective binding of less polar or more polar compounds by the use of normal phase chromatography on, for example, silica.

In addition, an affinity matrix that binds specifically to the product or excess reactant may be used. Examples of available affinity matrices include resins containing organomercurial groups that bind to thiol groups, or matrices bearing boronate residues which adsorb compounds containing groups such as cis-hydroxyl groups.

In another preferred embodiment, particularly useful in the COMBISYN® matrix device, the reaction mixture is transferred to a work station at which the two liquid phases are separated. Transfer may take place, for example, by pumping the reaction mixture from the reaction vessel to the work station, or by automated or manual movement of the reaction vessel to the work station. Either the liquid phase containing the unreacted reactants can be removed and discarded, or the liquid phase containing the desired product can be recovered. After the recovery step, the liquid phase containing the desired product can then be returned to the reaction vessel.

If the recovery step has increased the volume of the liquid phase, or if it is otherwise desired to reduce the volume of the liquid phase, the volume of the liquid phase can be reduced with, e.g., evaporative methods such as drying under a stream of air or N2.

In a third preferred embodiment, this invention features the combinatorial library produced by the preferred method of combinatorial synthesis using a template having two or more functionalization sites. In a more preferred embodiment, the library will consist of the compounds shown in FIGS. 6A–AA or the compounds produced by using the reactants shown in Table 2.

The compounds of a library will contain the common scaffold group provided by the template. A "scaffold" group is a chemical group, or core molecule, which is common to all of the compounds in the library, and to which other functional groups have been added during synthesis of the library. The functional groups may be the same or different from each other. The compounds in the libraries can be screened for the discovery of pharmaceutical drugs or other useful chemicals, such as veterinary drugs, diagnostic reagents, pesticides, herbicides, novel materials, or compounds with other biological activities.

As used herein, the term "alkyl" refers to an aliphatic hydrocarbon group or compound, preferably a saturated hydrocarbon, either unbranched or branched. The alkyl group may be optionally substituted with one or more chemical groups or functionalization sites which are attached commonly to such chains, preferably hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, and the like. The alkyl group may be cyclic or acyclic. An alkane is a compound containing an alkyl group.

An "aryl" group is any aromatic group with a substituent group attached directly to a ring carbon. The aryl group may be substituted with one or more functionalization sites which are attached commonly to such compounds, such as hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, sulfonyl, and the like.

A "heterocyclic" group contains a ring made up of carbon atoms and at least one other type of atom, for example, nitrogen, oxygen, or sulfur. The heterocyclic product may be aromatic or saturated.

The term "alkoxyl" denotes the group —OR, where R is alkyl as defined above, such as methoxy, ethoxy, n-propoxy, iso-propoxy, n-butoxy, sec-butoxy, iso-butoxy, or tert-butoxy and the like.

A "cyclic molecule" is a molecule which has at least one chemical moiety which forms a ring. The ring may contain three atoms or more. The molecule may contain more than one cyclic moiety, the cyclic moieties may be the same or different.

An "aryl" group is a group which contains at least one aromatic ring.

An "acyclic" group does not contain a ring structure. However, the molecule may be straight or branched.

A carbon-hetero multiple bond is a multiple bond between a carbon atom and a second type of atom. Examples of carbon-hetero multiple bonds are carbon-nitrogen double bonds, carbon-nitrogen triple bonds, carbon-sulfur double bonds, or carbon-oxygen double bonds. Examples of compounds containing carbon-oxygen double bonds are carboxylic acids, ketones, aldehydes, amides, esters, and thioesters.

Preferably the synthesis will be automated. An "automated" method of synthesis is one in which a self-operating device is used to deliver at least one of the reactants to more than one reaction vessel, and to simultaneously carry out parallel multiple reactions, each in a separate reaction vessel. Each of the reactants delivered may be the same or a different reactant. The "self-operating device" is one which does not require manual manipulation for the delivery of the reactant to each reaction vessel. Delivery is the physical transfer of a reactant from a container to the reaction vessel. Preferably the number of simultaneous reactions will be greater than 2 and less than 100. Even more preferably the number of simultaneous reactions will be eight or more reactions. In addition, two or more sets of simultaneous reactions can be carried out as part of one automated "reaction step" in a chemical synthesis of a library of compounds. The different sets of simultaneous reactions may have the same or a different starting time.

Pharmacological Compound Screening

The combinatorial libraries of the present invention may be screened for pharmacologically active compounds. Combinatorial library compounds that bind to individual cellular receptors, or functional portions of the individual cellular receptor (and may additionally be capable of disrupting receptor function) may be identified.

One such method for identifying an agent to be tested for an ability to bind to and potentially modulate a cellular receptor signal transduction pathway is as follows. The method involves exposing at least one compound from the combinatorial libraries of the present invention to a protein comprising a functional portion of a cellular receptor for a time sufficient to allow binding of the combinatorial library compound to the functional portion of the cellular receptor; removing non-bound compound; and determining the presence of the compound bound to the functional portion of the cellular receptor, thereby identifying a compound to be tested for an ability to modulate a cellular receptor signal transduction pathway.

One method utilizing this approach that may be pursued in the isolation of such receptor-binding molecules would include the attachment of a combinatorial library molecule, or a portion thereof, to a solid matrix, such as agarose or plastic beads, microtiter wells, petri dishes, or membranes composed of, for example, nylon or nitrocellulose, and the subsequent incubation of the attached combinatorial library molecule in the presence of a potential combinatorial library molecule-binding compound or compounds. Attachment to said solid support may be direct or by means of a combinatorial-library-compound-specific antibody bound directly to the solid support. After incubation, unbound compounds are washed away, component-bound compounds are recovered. By utilizing this procedure, large numbers of types of molecules may be simultaneously screened for receptor-binding activity.

Pharmaceutical Administration

When used as a therapeutic the compounds isolated from the combinatorial library of the present invention are preferably administered with a physiologically acceptable carrier. The compounds can be prepared as pharmaceutically acceptable salts (ie, non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See, e.g., supra. PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipient can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents. The compounds or pharmaceutical composition can be administered by different routes including intravenously, intraperitoneally, subcutaneously, and intramuscularly; orally, topically, or transmucosally.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, many small organic molecules may be directly administered intracellularly.

Pharmaceutical compositions suitable for use in the present invention include compositions wherein the active ingredients are contained in an effective amount to achieve its intended purpose. Determination of the effective amounts is within the capability of those skilled in the art, especially in light of the detailed disclosure provided herein.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For any compound used in the method of the invention, the therapeutically effective does can be estimated initially from cell culture and animal models. For example, a dose can be formulated in animal models to achieve a circulating concentration range that includes the $IC_{50}$ as determined in cell culture. Such information can be used to more accurately determine useful doses in humans.

A preferred physiological carrier is PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water.

The use of hydrophobic compounds can be facilitated by different techniques such as combining the compound with a carrier to increase the solubility of the compound and using frequent small daily doses rather than a few large daily doses. For example, the composition can be administered at short time intervals, such as by the methods described above or using a pump to control the time interval or achieve continuous administration. Suitable pumps are commercially available (e.g, the ALZET® pump sold by Alza corporation, and the BARD ambulatory PCA pump sold by Bard MedSystems).

The proper dosage depends on various factors such as the type of disease being treated, the particular composition being used, and the size and physiological condition of the patient. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/-day, most preferably 0.2 to 15 mg/kg/day. Alternatively, drugs can be administered at 0.5 to 1200 mg/m$^2$/day, preferably 0.5 to 150 mg/m$^2$/day, most preferably 5 to 100 mg/m$^2$/day. The average plasma level should be 50 to 5000 µg/ml, preferably 50 to 1000 µg/ml, and most preferably 100 to 500 µg/ml. Plasma levels may be reduced if pharmacological effective concentrations of the drug are achieved at the site of interest.

Herein, we detail a high purity solution phase parallel synthesis of a combinatorial library employing a general or template which implements one such simple purification protocol at each step.

EXAMPLE 1

Use of the Template in the Synthesis of a Combinatorial Library

A 27-member combinatorial library constructed as a 3×3×3 matrix having 27 members was synthesized according to the scheme in FIG. 4, using the template shown in FIG. 3.

As used herein, EDCI refers to 1-(3-Dimethylaminopropyl)-3-ethylcarbodiimide hydrochloride. The term PyBOP refers to benzotriazole-1-yl-oxy-tris-pyrrolidinophosphonium hexafluorophosphate. EtOAC refers to ethanol acetate. DMF refers to N,N-dimethylformamide. i-$Pr_2$NEt refers to N,N-diisopropylisoamine.

Each of the expected library members was obtained in a purified form ($\geq$90–100%) irrespective of the reactions efficiencies in amounts ranging from 5–60 mg without prior optimization. In situ closure of N-BOC-iminodiacetic acid to the anhydride 1 (1 equivalent EDCI, DMF, 25° C., 1 hour) followed by treatment with one of three $R^1NH_2$ (1 equivalent, DMF, 25° C., 20 hours, 84–86%) cleanly afforded the monoamides which were purified by simple acid extraction to remove unreacted $R^1NH_2$, EDCI, and its reaction byproducts. With the template shown in FIG. 1, the first derivatiziation with a primary amine proved sufficiently effective that the deliberate aqueous base dissolution of the desired product was not required for isolation of pure product. In the instances of the use of a neutral nucleophile ($R^1$OH, $R^1$SH, $R^1$-Met) in this first functionalization, the purification has been effectively accomplished by removal of the coupling reagent (EDCI) and its byproducts by dissolution in 10% aqueous HCl, extraction of the product carboxylic acid into 10% aqueous NaOH for the removal of neutral reactants, and reacidification and extraction into EtOAc or $CH_2Cl_2$ for product isolation. The three monoamides were each partitioned into three portions with one smaller portion being retained for archival purposes. Each of the equal three portions were treated with three $R^2NH_2$ (1 equivalent, and PyBOP (1 equivalent, 2 equivalent i-$Pr_2$NEt, DMF, 20° C., 25 hours, 65–99%) to afford nine diamides which were effectively purified by acid and base extractions of the unreacted $R^2NH_2$, PyBOP and its reaction byproducts. In the instances of the use of neutral nucleophiles ($R^2$OH, $R^2$SH, $R^2$-Met) in this second functionalization, the further purification of the neutral reactants from the desired products was readily accomplished upon N-BOC deprotection and aqueous acid extraction of the resulting secondary amine. Following the second functionalization and N-BOC deprotection (4N HCl, dioxane, 25° C., 45 minutes), reaction of three equal portions of each amine with three $R^3CO_2H$ (1 equivalent) in the presence of PyBOP (1 equivalent, 3 equivalents i-$Pr_2$NEt, DMF, 25° C., 20 hours, 16–100%) provided 27 agents which were purified by aqueous acid and base extractions to remove unreacted starting materials, reagents, and their reaction byproducts. Overall yields for the 27 agents ranged from 9–84% with an average overall yield of 61% for the three derivatizations. Importantly, and irrespective of individual yields, all intermediates and final products were $\geq$90% pure with most being >95% pure. Without optimization, and in the first experiment, most of the final library products were obtained in 32–60 mg quantities as individual identified samples at this exceptional level of purity ($\geq$95%) suitable for direct use in screening efforts withouT further purification.

Reaction schemes employing larger targeted libraries with matrix characterization of each reaction type, automated synthesis, additional combinatorial chemistry library templates, as well as additional approaches to the solution phase synthesis of chemical libraries are within the scope of this invention. [31].

EXAMPLE 2

General Procedure for the Preparation of N-((tert-Butyloxy)carbonyl)iminodiacetic Acid Monoamides.

A solution of N-((tert-butyloxy)carbonyl)iminodiactic acid (0.349 g, 1.50 mmol) in DMF (15 mL) was treated with EDCI (0.294 g, 1.54 mmol) at 25° C. The mixture was stirred at 25° C. for 1 hour before the primary amine ($R^1NH_2$, 1 equivalent) was added and the solution was stirred for 20 hours at 25° C. The reaction mixture was poured into 10% aqueous HCl (60 mL) and extracted with ethanol acetate (100 mL). The organic phase was washed with 10% HCl (40 mL) and saturated aqueous NaCl (2×50 mL), dried ($Na_2SO_4$), filtered and concentrated in vacuo to yield the pure N-((tert-butyloxy)carbonyl)iminodiacetic acid monoamides. The following results were obtained for the three products of this reaction.

N'-((tert-Butyloxy)carbonyl)-N-benzyliminodiacetic Acid Monoamide (FIG. 4A): 417 mg (86%); 1H NMR (CD3OD, 300 MHz) 6 7.28 (m, SH), 4.40 (br s, 2H), 4.04, 4.01, 3.98, and 3.93 (four s, total 4H), 1.40 and 1.32 (two s, total 9H); FABHRMS (NBA) m/e 323.1615 (M+$H^+$, $C_{16}H_{23}N_2O_5$ requires 323.1607).

N'-((tert-Butyloxy) carbonyl)-N-(n-butyl) iminodiacetic Acid Monoamide (FIG. 4B): 362 mg (84%); 1HNMR (CD3OD, 300 MHz) δ 4.04 and 4.00 (two s, total 2H), 3.92 and 3.89 (two s, total 2H), 3.22 (m,2H), 1.55–1.31 (m, 4H), 1.42 (s, 9H), 0.95–0.89 (m, 3H); FABHRMS (NBA) m/e 289.1769 (M+$H^+$, $C_{13}H_{25}N_2O_5$ requires 289.1763)

N'-((tert-Butyloxy)carbonyl)-N-cyclohexyliminodiacetic Acid Monoamide (FIG. 4C): 402 mg (85%); 1HNMR (CD3OD, 300 MHz) δ 4.03 and 3.99 (two s, total 2H), 3.90 and 3.87 (two s, total 2H), 3.68 (m, 1H), 1.90–1.20 (m, 10H), 1.42 (s, 9H); FABHRMS (NBA) m/e 315.1928 (M+$H^+$, $C_{15}H_{27}N_2O_5$ requires 315.1920).

EXAMPLE 3

General Procedure for the Second Derivatization:

Each of the N-((tert-butyloxy)carbonyl)iminodiacetic acid monoamides was dissolved in anhydrous DMF (20 mL/mmol) and was divided into three equal portions in three separate vials. Each solution was treated with one of three primary amines ($R^2NH_2$, 1 equivalent), diisopropyl ethylamine (2 equivalents) and of PyBOP (1 equivalent) The solution (20 mL DMF/mmol) was stirred at 25° C. for 20 hours. The mixture was poured into 10% aqueous HCl and extrated with EtOAc. The organic phase was washed with 10% aqueous HCl, saturated aqueous NaCl, 5% aqueous $NaHCO_3$, and saturated aqueous NaCl. The organic layer was dried ($Na_2SO_4$), filtered and concentrated in vacuo to yield the diamides (65–99%). The following results were obtained for each of the products of this reaction.

N'-(tert-Butyloxy)carbonyl)-N-(4-sec-butylphenyl)-N-cyclohexyliminodiacetic Acid Diamide (FIG. 5A): 198 mg (99%); $^1$H NMR ($CDCl_3$, 300 MHz) δ 9.60 (m, 1H), 7.63 (d, J =8.0 Hz, 2H), 7.15 (d, J =8.0 Hz, 2H), 6.61 and 5.80 (two m, total 1H), 4.03 and 3.95 (two s, total 2H), 3.90 and 3.84 (two s, total 2H), 2.57 (m, 1H), 2.0–1.55 (m, 8H), 1.45 and 1.41 (two s, total 9H), 1.22 (d, J=6.9 Hz, 3H), 0.82 (t, J =7.2 Hz, 3H); FABHRMS (NBA) m/e 446.3005 (M+$H^+$, $C_{25}H_{40}N_3O_4$ requires 446.3019).

N'-((tert-Butyloxy)carbonyl)-N-cyclohexyl-N-(3-methoxypropyl)iminodiacetic Acid Diamide (FIG. 5B): 135 mg (88%); $^1$H NMR ($CDCl_3$, 300 MHz) δ 7.98 (m, 1H) , 6.99 and 6.82 (two m, total 1H), 3.84 and 3.79 (two s, total 4H), 3.47 (t, J =5.9 Hz, 2H), 3.43–3.39 (m, 2H), 3.34 (s, 3H), 1.92–1.15 (m, 10H), 1.43 (s, 9H); FABHRMS (NBA-CsI) m/e 518.1647 (M+$Cs^+$, $C_{19}H_{35}N_3O_5Cs$ requires 518.1631).

N'-((tert-Butyloxy)carbonyl)-N-cyclohexyl-N-(2,2-diphenylethyl)iminodiacetic Acid Diamide (FIG. 5C): 197 mg (82%); $^1$H NMR ($CDCl_3$, 300 MHz) δ 7.90 and 6.85

(two t, total 1H), 7.78 and 6.78 (two d, total 1H), 7.26 (m, 10H), 4.26 (m, 1H), 3.95, 3.94, 3.93 and 3.91 (four s, total 4H), 3.72 and 3.70 (two s, total 2H), 3.15 (m, 1H), 1.92–1.61 (m, 4H), 1.40 and 1.33 (two s, total 9H), 1.29–1.21 (m, 6H); FABHRMS (NBA-CsI) m/e 626.2023 (M+Cs$^+$, $C_{29}H_{39}N_3O_4$Cs requires 626.1995).

N'-((tert-Butyloxy)carbonyl)-N-benzyl-N-(4-sec-butylphenyl)iminodiacetic Acid Diamide (FIG. 5D): 180 mg (99%); $^1$H NMR (CDCl$_3$, 300 MHz) δ 9.43 (br s, 1H), 7.61 (d, J =8.3 Hz, 1H), 7.52 (d, J =8.0 Hz, 1H), 7.30 (br s, 5H), 7.13 (d, J =8.2 Hz, 2H), 6.60 (t, 1H), 4.52 and 4.50 (two s, total 2H), 4.01, 3.95 and 3.89 (three s, total 4H), 2.56 (m, 1H), 1.57 (m, 2H), 1.40 and 1.36 (two s, total 9H), 1.21 (d, J =6.8 Hz, 3H), 0.81 (t, J =7.4 Hz, 3H); FABHRMS (NBA-CsI) m/e 586.1662 (M+Cs$^+$, $C_{26}H_{35}N_3O_4$Cs requires 586.1682).

N'-((tert-Butyloxy)carbonyl)-N-benzyl-N-(3-methoxypropyl)iminodiacetic Acid Diamide (FIG. 5E): 141 mg (90%); $^1$H NMR (CDCl$_3$, 300 MHz) δ 8.82, 7.85, 7.58 and 6.90 (four br s, total 2H), 7.30 (m, 5H), 4.49 and 4.47, (two s, total 2H), 3.90 and 3.86 (two s, total 2H), 3.84 and 3.81 (two s, total 2H), 3.46 (t, J =5.8 Hz, 2H), 3.32 (s, 3H), 3.14 (m, 2H), 1.80 (m, 2H), 1.42 and 1.35 (two s, total 9H); FABHRMS (NBA-CsI) m/e 526.1335 (M+Cs$^+$, $C_{20}H_{31}N_3O_5$Cs requires 526.1318).

N'-((tert-Butyloxy)carbonyl)-N-benzyl-N-(2,2-diphenylethyl)iminodiacetic Acid Diamide (FIG. 5F): 212 mg (99%); $^1$H NMR (CDCl$_3$, 300 MHz) δ 8.50, 7.78 and 6.50 (three br s, total 2H), 7.33–7.21 (m, 15H), 4.47 and 4.45 (two s, total 2H), 3.93–3.89 (m, 2H), 3.72–3.67 (m, 2H), 3.15 (m, 1H), 1.32 (s, 9H); FABHRMS (NBA-CsI) m/e 634.1664 (M+Cs$^+$, $C_{30}H_{35}N_3O_4$Cs requires 634.1682).

N'-((tert-Butyloxy)carbonyl)-N-(n-butyl)-N-(4-sec-butylphenyl)iminodiacetic Acid Diamide (FIG. 5G): 137 mg (99%); $^1$H NMR (CDCl$_3$, 300 MHz) δ 9.60 (br s, 1H), 7.61, 7.52, 7.13 (three d, J =8.2 Hz, total 4H), 6.32 (br s, 1H), 4.02, 3.95, 3.91 and 3.86 (four s, total 4H), 3.32 (m, 2H), 2.56 (m, 1H), 1.81–1.48 (m, 6H), 1.43 and 1.40 (two s, total 9H), 1.22 (m, 3H), 0.93 (t, J =7.3 Hz, 3H), 0.81 (t, J =7.2 Hz, 3H); FABHRMS (NBA-CsI) m/e 552.1823 (M+Cs$^+$, $C_{23}H_{37}N_3O_4$Cs requires 552.1838).

N'-((tert-Butyloxy)carbonyl)-N-(n-butyl)-N-(3-methoxypropyl)iminodiacetic Acid Diamide (FIG. 5H): 75 mg (65%); $^1$H NMR (CD$_3$OD, 300 MHz) δ 3.90 and 3.88 (two s, total 4H), 3.43 (m, 2H), 3.31 and 3.29 (two s, total 3H), 3.22 (m, 2H), 1.86–1.74 (m, 4H), 1.41 (s, 9H), 0.93 (m, 3H); FABHRMS (NBA-CsI) m/e 492.1461 (M+Cs$^+$, $C_{17}H_{33}N_3O_5$Cs requires 492.1475).

N'-((tert-Butyloxy)carbonyl)-N-(n-butyl)-N-(2,2-diphenylethyl)iminodiacetic Acid Diamide (FIG. 5I): 155 mg (99%); $^1$H NMR (CD$_3$OD, 300 MHz) δ 7.27–7.15 (m, 10H), 4.30 (t, J =7.7 Hz, 1H), 3.86 and 3.83 (two s, total 2H), 3.81 and 3.77 (two s, total 2H), 3.30 (m, 2H), 3.21 (t, 6.8 Hz, 2H), 1.56–1.42 (m, 2H), 1.37 and 1.30 (two s, total 9H), 0.96 and 0.95 (two t, J =7.2 Hz, total 3H): FABHRMS (NBA-CsI) m/e 600.1821 (M+Cs$^+$, $C_{27}H_{37}N_3O_4$Cs requires 600.1838).

EXAMPLE 4

General Procedure for the Third Derivatization:

Each of the N'-((tert-butyloxy)carbonyl)-N,N-disubstituted iminodiacetic acid diamides was dissolved in 4N HCl-dioxane (32 mL/mmol) and the mixture was stirred at 25° C. for 45 min. The solvent was removed in vacuo and the residue was dissolved in anhydrous DMF (28 mL/mmol) and was divided into three equal portions and placed in three separate vials. The solution was treated with one of three carboxylic acids (R$^3$CO$_2$H, 1 equiv) followed by diisopropyl ethylamine (3 equiv) and PyBOP (1 equiv). The solution was stirred for 20 h at 25° C. The mixture was poured into 10% aqueous HCl and extracted with EtOAc. The organic phase was washed with 10% aqueous HCl and extracted with EtOAc. The organic phase was washed with 10% aqueous HCl, saturated aqueous NaCl, 5% aqueous NaHCO$_3$ and saturated aqueous NaCl. The organic phase was dried (Na$_2$SO$_4$), filtered and concentrated in vacuo to yield the final products (16–100%). The following results were obtained for each of the products of this reaction.

N'-Benzylcarbonyl-N-cyclohexyl-N-(2,2-diphenylethyl) iminodiacetic Acid Diamide (FIG. 6A): 47 mg (86%); $^1$H NMR (CDCl$_3$, 300 MHz) δ 9.10 and 8.75 (two m, total 1H), 7.50–7.05 (m, 15H), 6.10 and 5.95 (two m, total 1H), 4.40 and 4.18 (two t, J =8.4 Hz, total 1H), 3.91 (m, 2H), 3.82 and 3.73 (two s, total 2H), 3.61 and 3.58 (two s, total 2H), 3.21 (br s, 2H), 1.93–1.14 (m, 10H); FABHRMS (NBA) m/e 512.2907 (M+H$^+$, $C_{32}H_{38}N_3O_3$ requires 512,2913).

N'-Benzoyl-N-cyclohexyl-N-(2,2-diphenylethyl) imino-diacetic Acid Diamide (FIG. 6B): 37 mg (69%); $^1$H NMR (CDCl$_3$, 300 MHz) δ 9.18 and 6.40 (two br s, total 1H), 8.35 and 6.05 (two m, total 1H), 7.38–7.21 (m, 15H), 4.48 and 4.22 (two t, J =8.4 Hz, total 1H), 3.99 (m, 2H), 3.89–3.84 (m, 2H), 3.13 (m, 2H), 2.04–1.20 (m, 10H); FABHRMS (NBA) m/e 498.2759 (M+H$^+$, $C_{31}H_{36}N_3O_3$ requires 498.2756).

N'-Ethylcarbonyl-N-cyclohexyl-N-(2,2-diphenylethyl) iminodiacetic Acid Diamide (FIG. 6C): 39 mg (81%); $^1$H NMR (CDCl$_3$, 400 MHz) δ 9.27 and 6.05 (two t, total 1H), 8.80 and 5.87 (two d, J 7.3 Hz, total 1H), 7.37–7.15 (m, 10H), 4.38 and 4.16 (two t, J =8.4 Hz, total 1H), 3.89 and 3.84 (two s, total 2H), 3.76 and 3.62 (two s, total 2H), 3.15 (m, 2H), 2.25 (q, J =7.3 Hz, 2H), 1.95–1.07 (m, 10H), 0.88 (t, J =7.4 Hz, 3H); FABHRMS (NBA) m/e 450.2749 (M+H$^+$, $C_{27}H_{36}N_3O_3$ requires 450.2756).

N'-Benzylcarbonyl-N-benzyl-N-(3-methoxypropyl) imi-nodiacetic Acid Diamlide (FIG. 6D): 28 mg (76%); $^1$H NMR (CDCl$_3$, 300 MHz) δ 9.61 and 8.71 (two t, total 1H), 7.12–7.37 (m, 10H), 6.89 and 6.85 (two t, total 1H), 4.43–4.40 (m, total 2H), 4.04 and 4.00 (two s, total 2H), 3.89 and 3.84 (two s, total 2H), 3.64 and 3.58 (two s, total 2H), 3.42 (t, J =6.7 Hz, 2H), 3.30 (s, 3H), 3.13 (t, J =3.5 Hz, 2H), 1.82–1.72 (m, 2H); FABHRMS (NBA) m/e 412.2231 (M+H$^+$, $C_{23}H_{30}N_3O_4$ requires 412.2236).

N'-Benzoyl-N-benzyl-N-(3-methoxypropyl) iminodiacetic Acid Diamide (FIG. 6E): 24 mg (67%); $^1$H NMR (CDCl$_3$, 300 MHz) δ 9.35 and 8.46 (two br s, total 1H), 7.42–7.20 (m, 10H), 6.98 (br s, 1H), 4.49 (d, J =5.7 Hz, 2H), 4.00 (m, 4H), 3.47–3.31 (m, 5H), 3.13 (m, 2H), 1.80 (m, 2H); FABHRMS (NBA) m/e 398.2077 (M+H$^+$, $C_{22}H_{28}N_3O_4$ requires 398.2079).

N'-Ethylcarbonyl-N-benzyl-N-(3-methoxypropyl) imino-diacetic Acid Diamide (FIG. 6F): 15 mg (48%); $^1$H NMR (CDCl$_3$, 300 MHz) δ 9.75 and 8.90 (two t, total 1H), 7.30–7.26 (m, 5H), 6.85 and 6.65 (two t, total 1H), 4.47 and 4.46 (two d, J =17.8 Hz, 2H), 4.03 and 4.00 (two s, total 2H), 3.94 and 3.88 (two s, total 2H), 3.48–3.34 (m, 2H), δ 3.32 and 3.31 (two s, total 3H), 3.16 (m, 2H), 2.26 (m, 2H), 1.86–1.74 (m, 2H), 1.07 (m, 3H); FABHRMS (NBA) m/e 350.2054 (M+H$^+$, $C_{18}H_{28}N_3O_4$ requires 350.2079).

N'-Benzylcarbonyl-N-benzyl-N-(2,2-diphenylethyl) imi-nodiacetic Acid Diamide (FIG. 6G): 52 mg (88%); $^1$H NMR (CDCl$_3$, 300 MHz) δ 9.38 and 9.00 (two t, total 1H), 7.32–7.18 (m, 20H), 6.42 and 5.98 (two t, total 1H), 4.44–4.36 (m, 2H), 3.95–3.84 (m, 2H), 3.82 and 3.72 (two s, total 2H), 3.62 and 3.55 (two s, total 2H), 3.20 (s, 2H), 3.16–3.11 (m, 2H); FABHRMS (NBA) m/e 520.2606 (M+H$^+$, C$_{33}$H$_{34}$N$_3$O$_4$ requires 520.260).

N'-Benzoyl-N-benzyl-N-(2,2-diphenylethyl) iminodiacetic Acid Diamide (FIG. 6H): 49 mg (86%); $^1$H NMR (CD$_3$OD, 300 MHz) δ 9.00 (m, 1H), 7.36–7.14 (m, 20H), 6.75 (m, 1H), 4.45 (br s, 2H), 4.05–3.83 (m, 4H), 3.30 (m, 2H); FABHRMS (NBA) m/e 506.2488 (M+H$^+$, C$_{32}$H$_{32}$N$_3$O$_3$ requires 506.2443).

N'-Ethylcarbonyl-N-benzyl-N-(2,2-diphenylethyl) iminodiacetic Acid Diamide (FIG. 6I): 45 mg (87%); $^1$H NMR (CDCl$_3$, 300 MHz) δ 9.50 and 9.25 (two t, total 1H), 7.35–7.16 (m, 15H), 6.95 and 6.30 (two t, total 1H), 4.46 (m, 2H), 4.36 and 4.15 (two t, J =8.4 Hz, total 1H), 3.94 and 3.82 (two s, total 2H), 3.75 and 3.68 (two s, total 2H), 3.15 (m, 2H), 2.20 (q, J =7.2 Hz, 2H), 1.02 and 0.87 (two t, J =7.2 Hz, total 3H); FABHRMS (NBA) m/e 458.2439 (M+H$^+$, C$_{28}$H$_{32}$N$_3$O$_3$ requires 458.2443).

N'-Benzylcarbonyl-N-(4-sec-butylphenyl)-N-cyclohexyliminodiacetic Acid Diamide (FIG. 6J): 57 mg (99%); $^1$H NMR (CDCl$_3$, 300 MHz) δ 9.38 and 8.50 (m, total 1H), 7.61 (d, J =8.5 Hz, 1H), 7.43 (d, J =8.5 Hz, 1H), 7.26–7.04 (m, 7H), 6.45 (m, 1H), 4.13 and 4.02 (two s, total 2H), 3.98 and 3.89 (two s, total 2H), 3.68 and 3.64 (two s, total 2H), 3.14 (m, 2H), 2.56 (m, 1H), 1.86–1.12 (m, 15H), 0.81 (t, J =7.2 Hz, 3H); FABHRMS (NBA) m/e 464.2893 (M+H$^+$, C$_{28}$H$_{38}$N$_3$O$_3$ requires 464.2913).

N'-Benzoyl-N-(4-sec-butylphenyl)-N-cyclohexyliminodiacetic Acid Diamide (FIG. 6K): 55 mg (98%); $^1$H NMR (CDCl$_3$, 300 MHz) δ 9.78 and 8.00 (m, total 1H), 7.05–7.66 (m, 9H), 4.15 and 4.10 (two s, total 2H), 4.04 and 4.00 (two s, total 2H), 3.78 (m, 2H), 2.55 (m, 1H), 1.16–1.81 (m, 14H), 0.81 (t, J =7.4 Hz, 3H) ; FABHRMS (NBA) m/e 450.2748 (M+H$^+$, C$_{27}$H$_{36}$N$_3$O$_3$ requires 450.2756).

N'-Ethylcarbonyl-N-(4-sec-butylphenyl)-N-cyclohexyliminodiacetic Acid Diamide (FIG. 6L): 54 mg (99%); $^1$H NMR (CDCl$_3$, 300 MHz) δ 11.30 and 9.56 (two br s, total 1H), 8.52 and 6.57 (two d, J =7.6 Hz, total 1H), 7.65, 7.58, 7.13 and 7.07 (four d, J =8.5 Hz, total 4H), 4.15 and 4.07 (two s, total 2H), 4.06 and 3.96 (two s, total 2H), 2.55 (m, 1H), 2.33 (m, 1H), 1.90–1.14 (m, 17H), 1.09 (t, J =7.2 Hz, 3H), 0.80 (t, J =7.2 Hz, 3H); FABHRMS (NBA) m/e 402.2747 (M+H$^+$, C$_{23}$H$_{36}$N$_3$O$_3$ requires 402.2756).

N'-Benzylcarbonyl-N-benzyl-N-(4-sec-butylphenyl) iminodiacetic Acid Diamide (FIG. 6M): 50 mg (99%); $^1$H NMR (CDCl$_3$, 300 MHz) δ 9.40 and 9.00 (two br s, total 1H), 7.58–7.04 (m, 14H), 4.38 and 4.36 (two s, total 2H), 4.07 and 4.02 (two s, total 2H), 3.91 and 3.88 (two s, total 2H), 3.63 and 3.54 (two s, total 2H), 2.55 (m, 1H), 1.55 (m, 2H), 1.21 and 1.18 (two d, J =6.8 Hz, total 2H), 0.80 (t, J =7.1 Hz, 3H); FABHRMS (NBA) m/e 472.2603 (M+H$^+$, C$_{29}$H$_{34}$N$_3$O$_3$ requires 472.2600).

N'-Benzoyl-N-benzyl-N-(4-sec-butylphenyl) iminodiacetic Acid Diamide (FIG. 6N): 47 mg (97%) $^1$H NMR (CDCl$_3$, 300 MHz) δ 9.60 and 8.95 (two br s, total 1H), 8.70 (m, 1H), 7.44–7.12 (m, 14H), 4.48–4.10 (m, 4H), 3.59 (q, J =7.0 Hz, 2H), 1.58 (m, 2H), 1.19 (m, 3H), 0.80 (t, J =5.6 Hz, 3H); FABHRMS (NBA) m/e 458.2436 (M+H$^+$, C$_{28}$H$_{32}$N$_3$O$_3$ requires 458.2443).

N'-Ethylcarbonyl-N-benzyl-N-(4-sec-butylphenyl) iminodiacetic Acid Diamide (FIG. 6O): 41 mg (95%); $^1$H NMR (CDCl$_3$, 300 MHz) δ 9.40 and 9.20 (two t, total 1H), 7.64, 7.42, 7.12, 7.05 (four d, J =8.5 Hz, total 4H), 7.26 (br s, 5H), 4.46 (m, 2H), 4.09 and 4.05 (two s, total 2H), 4.03 and 3.98 (two s, total 2H), 1.20 (m, 3H), 1.07 and 1.01 (two t, J =7.5 Hz, total 3H), 0.80 and 0.79 (two t, J =7.4 Hz, total 3H); FABHRMS (NBA) m/e 410.2429 (M+H$^+$, C$_{24}$H$_{32}$N$_3$O$_3$ requires 410.2443).

N'-Benzylcarbonyl-N-(n-butyl)-N-(4-sec-butylphenyl) iminodiacetic Acid Diamide (FIG. 6P): 34 mg (98%); $^1$H NMR (CDCl$_3$, 300 MHz) δ 9.14 and 8.57 (two t, total 1H), 7.61, 7.43, 7.10, 7.06 (four d, J =8.2 Hz, total 4H), 7.22 (m, 5H), 4.13 and 4.05 (two s, total 2H), 3.99 and 3.91 (two s, total 2H), 3.69 and 3.65 (two s, total 2H), 3.23 (m, 2H), 2.55 (m, 1H), 1.59–1.14 (m, 6H), 1.20 (t, J =6.9 Hz, 3H), 0.88 (d, J =7.2 Hz, 3H), 0.81 (t, J =7.2 Hz, 3H); FABHRMS (NBA) m/e 438.2762 (M+H$^+$, C$_{26}$H$_{36}$N$_3$O$_3$ requires 438.2756)

N'-Benzoyl-N-(n-butyl)-N-(4-sec-butylphenyl) iminodiacetic Acid Diamide (FIG. 6Q); 30 mg (89%); $^1$H NMR (CDCl$_3$, 300 MHz) δ 9.10 and 8.85 (two br s, total 1H), 7.70–7.12 (m, 9H), 6.31 (m, 1H), 4.13–4.06 (m, 4H), 3.32 (m, 2H), 3.15–3.12 (m, 2H), 2.58 (m, 1H), 1.54 (m, 2H), 1.19 (m, 3H), 0.92 (t, J=7.0 Hz, 3H), 0.82 (t, J=7.2 Hz, 3H) ; FABHRMS (NBA) m/e 424.2607 (M+H$^+$, C$_{25}$H$_{34}$N$_3$O$_3$ requires 424.2600).

N'-Ethylcarbonyl-N-(n-butyl)-N-(4-sec-butylphenyl) iminodiacetic Acid Diamide (FIG. 6R): 30 mg (100%); $^1$H NMR (CDCl$_3$, 300 MHz) δ 11.33 and 9.30 (two br s, total 1H), 8.78 and 6.63 (two br s, total 1H), 7.66, 7.46, 7.14, 7.07 (four d, J =8.2 Hz, total 4H), 4.15, 4.07 and 3.98 (three s, total 4H), 3.27 (m, 2H), 3.15 (m, 1H), 2.54 (m, 1H), 2.34 (m, 2H), 1.83 (m, 1H), 1.59–1.25 (m, H), 1.19 (t, J =7.2 Hz, 3H), 1.09 (t, J =7.7 Hz, 3H), 0.89 (m, 3H), 0.80 (m, 3H); FABHRMS (NBA) m/e 376.2588 (M+H$^+$, C$_{21}$H$_{34}$N$_3$O$_3$ requires 376.2600).

N'-Benzylcarbonyl-N-cyclohexyl-N-(3-methoxypropyl) iminodiacetic Acid Diamide (FIG. 6S): 20 mg (60%); $^1$H NMR (CDCl$_3$, 300 MHz) δ 8.93 and 6.12 (two d, total 1H), 8.82 and 6.60 (two t, total 1H), 7.30–7.22 (m, 5H), 4.00 (s, 2H), 3.85 (s, 2H), 3.66 and 3.65 (two s, 2H), 3.48–3.38 (m, 2H), 3.32 (s, 3H), 3.16 (m, 1H), 1.86–1.10 (m, 10H); FABHRMS (NBA) m/e 404.2550 (M+H$^+$, C$_{22}$H$_{34}$N$_3$O$_4$ requires 404.2549).

N'-Benzoyl-N-cyclohexyl-N-(3-methoxypropyl) iminodiacetic Acid Diamide (FIG. 6T): 14 mg (43%); $^1$H NMR (CDCl$_3$, 300 MHz) δ 8.68 (m, 1H), 7.46–7.26 (m, 5H), 6.78 and 6.35 (two m, 1H), 3.98 (s, 2H), 3.95 (s, 2H), 3.52–3.34 (m, 2H), 3.33 (s, 3H), 3.14 (m, 1H), 1.90–1.10 (m, 12H); FABHRMS (NBA) m/e 390.2364 (M+H$^+$, C$_{21}$H$_{32}$N$_3$O$_4$ requires 390.2392).

N'-Ethylcarbonyl-N-cyclohexyl-N-(3-methoxypropyl) iminodiacetic Acid Diamide (FIG. 6U): 6 mg (21%); $^1$H NMR (CDCl$_3$, 300 MHz) δ 4.00 and 3.98 (two s, 2H), 3.87 (br s, 2H), 3.85–3.36 (m, 5H), 3.34 (s, 3H), 3.16 (m, 2H), 2.30 (q, J =7.2 Hz, 2H), 1.88–1.18 (m, 12H), 1.11 (t, J =7.2 Hz, 3H); FABHRMS (NBA) m/e 342.2407 (M+H$^+$, C$_{17}$H$_{32}$N$_3$O$_4$ requires 342.2392).

N'-Benzylcarbonyl-N-(n-butyl)-N-(2,2-diphenylethyl) iminodiacetic Acid Diamide (FIG. 6V): 38 mg (89%); $^1$H NMR (CDCl$_3$, 300 MHz) δ 9.05 and 8.90 (two t, total 1H), 7.29–7.18 (m, 15H), 6.20 and 6.10 (two t, total 1H), 4.38 and 4.16 (two t, J =7.7 Hz, total 1H), 3.92 (br s, 2H), 3.82 and 3.72 (two s, total 2H), 3.61 (s, 2H), 3.25–3.12 (m, 2H), 1.51–1.32 (m, 4H), 0.94 and 0.93 (two t, J =7.2 Hz, 3H); FABHRMS (NBA) m/e 486.2765 (M+H$^+$, C$_{30}$H$_{36}$N$_3$O$_3$ requires 486.2756).

N'-Benzoyl-N-(n-butyl)-N-(2,2-diphenylethyl) iminodiacetic Acid Diamide (FIG. 6W): 34 mg (80%); $^1$H NMR (CDCl$_3$, 300 MHz) δ 9.05 and 8.50 (two br s, total 1H), 7.37–7.14 (m, 15H), 6.50 and 6.30 (two br s, total 1H), 4.44 and 4.22 (two t, J =7.7 Hz, total 1H), 3.97 (m, 2H), 3.87 and 3.83 (two s, total 2H), 3.30 (q, J =6.2 Hz, 2H), 1.53–1.35 (m, 4H), 0.94 (t, J =7.1 Hz, 3H): FABHRMS (NBA) m/e 472.2581 (M+H$^+$, C$_{29}$H$_{34}$N$_3$O$_3$ requires 472.2600).

N'-Ethylcarbonyl-N-(n-butyl)-N-(2,2-diphenylethyl) iminodiacetic Acid Diamide (FIG. 6X): 32 mg (86%); $^1$H NMR (CDCl$_3$, 300 MHz) δ 9.21 and 9.00 (two t, total 1H), 7.33–7.16 (m, 10H), 6.18 and 6.12 (two t, total 1H), 4.38 and 4.19 (two t, J =7.7 Hz, total 1H), 3.91 and 3.84 (two s, total 2H), 3.76 and 3.65 (two s, total 2H), 3.27 (m, 2H), 3.15 (m, 1H), 2.26 (q, J =7.3 Hz, 2H), 1.87–1.81 (m, 4H), 1.56–1.32 (m, 4H), 1.09 (t, J =7.3 Hz, 3H), 0.87 (t, J =7.3 Hz, 3H); FABHRMS (NBA) m/e 424.2578 (M+H$^+$, C$_{25}$H$_{34}$N$_3$O$_3$ requires 424.2600).

N'-Benzylcarbonyl-N-(n-butyl)-N-(3-methoxypropyl) iminodiacetic acid Diamide (FIG. 6Y): 15 mg (70%); $^1$H NMR (CDCl$_3$, 300 MHz) δ 9.10 and 8.71 (two t, total 1H), 7.32–7.22 (m, 5H), 6.58 and 6.32 (two t, total 1H), 4.01 (s, 2H), 3.88 and 3.85 (two s, total 2H), 3.66 (s, 2H), 3.49–3.34 (m, 2H), 3.33 (s, 3H), 3.25–3.15 (m, 2H), 1.82–1.76 (m, 2H), 1.52–1.30 (m, 4H), 0.91 (t, J 7.0 Hz, 3H) ; FABHRMS (NBA) m/e 378.2406 (M+H$^+$, C$_{20}$H$_{31}$N$_3$O$_4$ requires 378.2392).

N'-Benzoyl-N-(n-butyl)-N-(3-methoxypropyl) iminodiacetic Acid Diamide (FIG. 6Z) : 10 mg (49%); $^1$H NMR (CDCl$_3$, 300 MHz) δ 8.95 and 8.50 (two br S, total 1H), 7.46–7.38 (m, 5H), 6.72 and 6.52 (two br s, total 1H), 3.98 (s, 4H), 3.47–3.42 (m, 2H), 3.33 and 3.31 (two s, total 3H), 3.16 (m, 1H), 1.85–1.79 (m, 2H), 1.70 (br s, 2H), 1.60–1.25 (m, 6H), 0.94 (t, J =7.7 Hz, 3H); FABHRMS (NBA) m/e 364.2236 (M+H$^+$, C$_{19}$H$_{30}$N$_3$O$_4$ requires 364.2236).

N'-Ethylcarbonyl-N-(n-butyl)-N-(3-methoxypropyl) iminodiacetic Acid Diamide (FIG. 6AA): 3 mg (16%) ; $^1$H NMR (CDCl$_3$, 300 MHz) δ 4.00 (br s, 2H), 3.87 (br S, 2H), 3.853–3.38 (m, 6H), 3.34 (s, 3H), 2.16 (q, J =7.2 Hz, 2H), 1.70–1.23 (m, H), 1.12 (t, J =7.3 Hz, 1H), 0.91 (t, J =6.6 Hz, 3H); FABHRMS (NBA) m/e 316.2245 (M+H$^+$, C$_{15}$H$_{30}$N$_3$O$_4$ requires 316.2236)

EXAMPLE 4

Construction of a 5×5×5 Combinatorial Library:

The reactants shown in Table 2 were used to construct a 5×5×5 library using the reactions described above. NMR data for representative members of first modified products are set forth below.

N'-((tert-Butyloxy)carbonyl)-N-(3,4-dimethoxyphenethyl)iminodiacetic acid monoamide: $^1$H NMR (CDCl$_3$, 300 MHz) δ 6.86–6.70 (m, 3H), 4.00, 3.93, 3.91, 3.88 (four s, total 4H), 3.819, 3.810 (two s, total 3H), 3.78 (s, 3H), 3.42 (m, 2H), s.76, 2.74 (two t, J=7.4 Hz, total 2H), 1.41, 1.37 (two s, total 9H).

N'-((tert-Butyloxy) carbonyl)-N-(5-indan)iminodiacetic acid monoamide: $^1$H NMR (CDCl$_3$, 300 MHz) δ 7.49–7.14 (m, 3H), 4.12, 4.08, 4.06, 4.01 (four s, total 4H), 2.88 (m, 4H), 2.07–1.97 (m, 2H), 1.44, 1.37 (two s, total 9H).

N'-((tert-Butyloxy)carbonyl)-N-(4-methylbenzyl) iminodiacetic acid monoamide: $^1$H NMR (CDCl$_3$, 300 MHz) δ 7.18–7.11 (m, 4H), 4.36 (br s, 2H), 4.04, 4.01, 3.98, 3.93 (four s, total 4H), 2.29 (br s 3H), 1.43, 1.33 (two s, total 9H).

N'-((tert-Butyloxy)carbonyl)-N-(2-methyoxyphenethyl) iminodiacetic acid monoamide: $^1$H NMR (CDCl$_3$, 300 MHz) δ 7.17–6.83 (m, 4H), 3.99, 3.91, 3.90, 3.87 (four s, total 4H), 3.82 (s, 3H), 3.41 (t, J =7.4 Hz, 2H), 2.82 (t, J =7.4 Hz, 2H), 1.42, 1.40 (two s, total 9H).

N'-((tert-Butyloxy)carbonyl)-N-(4-ethanolphenyl) iminodiacetic acid monoamide: $^1$H NMR (CDCl$_3$, 300 MHz) δ 7.50–7.15 (m, 4H), 4.13, 4.09, 4.07, 4.03 (four s, total 4H), 3.70 (m, 2H), 2.68 (m, 2H), 1.46, 1.40 (two s, total 9H).

The compounds shown in FIG. 7F–J have also been characterized by NMR (data not shown).

All patents and publications mentioned in this specification are indicative of the levels of those skilled in the art to which the invention pertains. All patents and publications are herein incorporated by reference to the same extent as if each individual publication is specifically and individually indicated to be incorporated by reference.

Other embodiments are within the following claims. Thus while several embodiments have been shown and described, various modifications may be made to the invention disclosed herein, without departing from the spirit and scope of the present invention.

What is claimed is:

1. A method of forming a multifunctional template utilizing a template of the structure below:

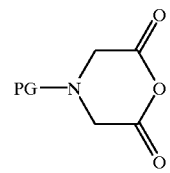

where PG is a protecting group, said method comprising the following steps:

(a) reacting, in solution, said template with at least one first reactant of the structure R$^1$XH wherein a first modified product of the formula below is formed

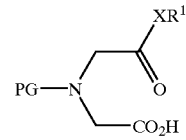

wherein said first reactant is selected from the group consisting of

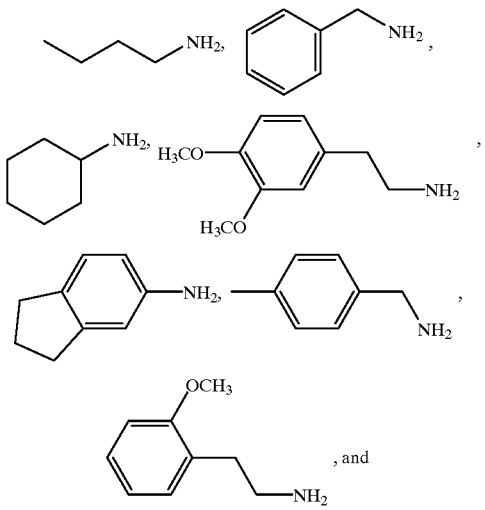

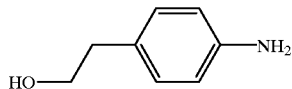

(b) separating said first modified product from unreacted first reactant;

(c) reacting, in solution, said first-modified product with a second reactant to form a second-modified product, wherein said second reactant is selected from the group consisting of;

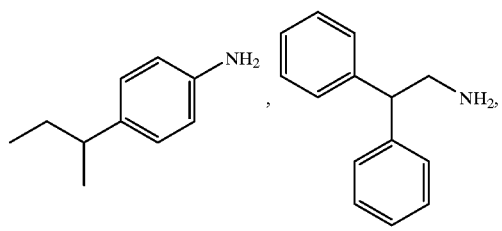

(d) separating said second-modified product from unreacted second reactant;

(e) reacting, in solution, said second-modified product with a third reactant to form a third-modified product, wherein said third reactant is selected from the group consisting of

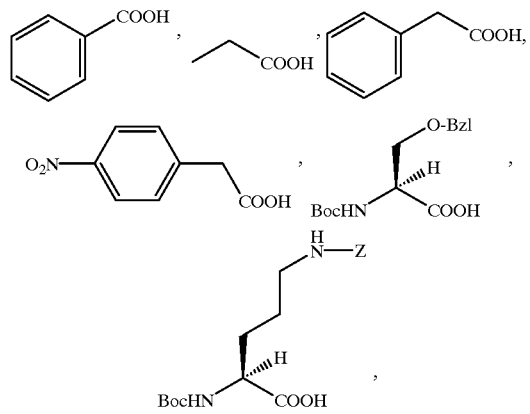

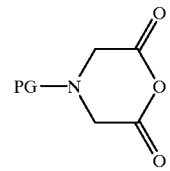

and (f) separating said third-modified product from unreacted third reactant.

2. A method of forming a multifunctional template utilizing a template of the structure below:

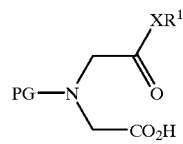

where PC is a protecting group, said method comprising the following steps:

(a) reacting, in solution, said template with at least one first reactant of the structure $R^1XH$ wherein a first modified product of the formula below is formed

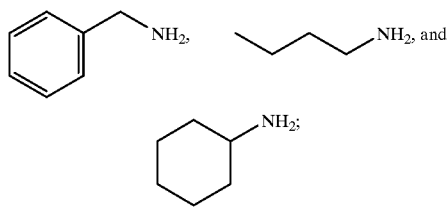

wherein said first reactant is selected from the group consisting of

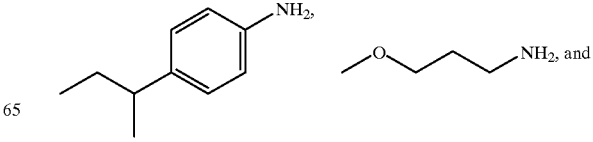

(b) separating said first modified product from unreacted first reactant;

(c) reacting, in solution, said first-modified product with a second reactant to form a second-modified product, wherein said second reactant is selected from the group consisting of;

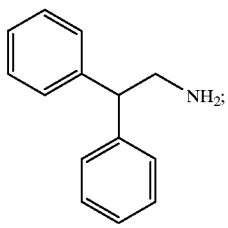

(d) separating said second-modified product from unreacted second reactant;

(e) reacting, in solution, said second-modified product with a third reactant to form a third-modified product, wherein said third reactant is selected from the group consisting of

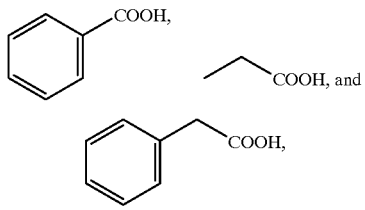

and (f) separating said third-modified product from unreacted third reactant.

3. A method of forming a multifunctional template utilizing a template of the structure below:

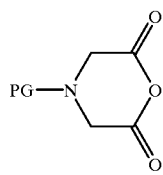

where PG is a protecting group, said method comprising the following steps:

(a) reacting, in solution, said template with at least one first reactant of the structure $R^1XH$ wherein a first modified product of the formula below is formed

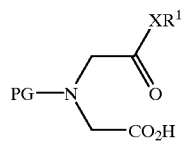

wherein said first reactant is selected from the group consisting of

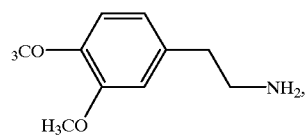

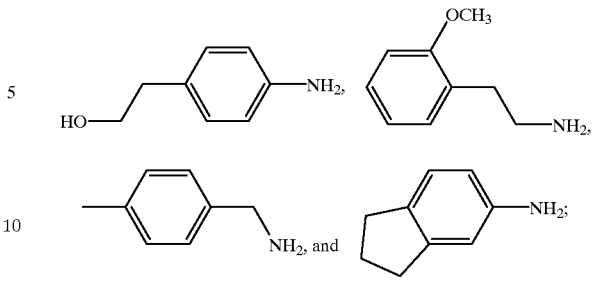

(b) separating said first modified product from unreacted first reactant;

(c) reacting, in solution, said first-modified product with a second reactant to form a second-modified product, wherein said second reactant is selected from the group consisting of;

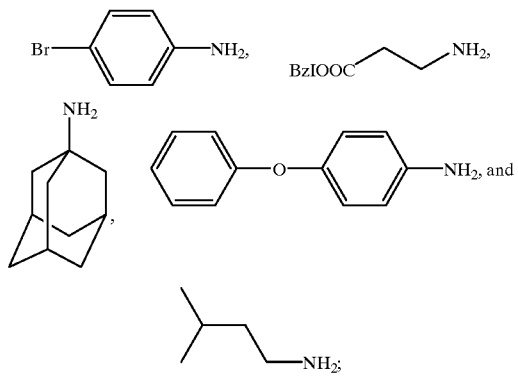

(d) separating said second-modified product from unreacted second reactant;

(e) reacting, in solution, said second-modified product with a third reactant to form a third-modified product, wherein said third reactant is selected from the group consisting of

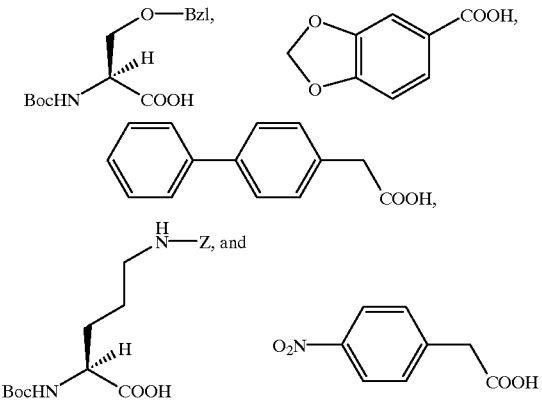

and (f) separating said third-modified product from unreacted third reactant.

* * * * *